United States Patent
Ferretti et al.

(10) Patent No.: US 10,966,978 B2
(45) Date of Patent: Apr. 6, 2021

(54) DOSE AND REGIMEN FOR HDM2-P53 INTERACTION INHIBITORS

(71) Applicant: Novartis AG, Basel (CH)

(72) Inventors: Stephane Ferretti, Huningue (FR); Nelson Guerreiro, Basel (CH); Sebastien Jeay, Niffer (FR); Astrid Jullion, Sierentz (FR); Christophe Meille, Sierentz (FR); Jens Wuerthner, Steinen (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/461,005

(22) PCT Filed: Nov. 14, 2017

(86) PCT No.: PCT/IB2017/057097
§ 371 (c)(1),
(2) Date: May 15, 2019

(87) PCT Pub. No.: WO2018/092020
PCT Pub. Date: May 24, 2018

(65) Prior Publication Data
US 2019/0298719 A1    Oct. 3, 2019

Related U.S. Application Data

(60) Provisional application No. 62/479,391, filed on Mar. 31, 2017, provisional application No. 62/422,144, filed on Nov. 15, 2016.

(51) Int. Cl.
| | | |
|---|---|---|
| *A61K 31/497* | (2006.01) |
| *A61K 31/505* | (2006.01) |
| *A61K 31/506* | (2006.01) |
| *A61P 7/00* | (2006.01) |
| *A61P 35/02* | (2006.01) |
| *A61K 45/06* | (2006.01) |
| *A61K 31/404* | (2006.01) |
| *A61K 31/4418* | (2006.01) |
| *A61K 31/4439* | (2006.01) |
| *A61P 35/00* | (2006.01) |
| *A61K 31/47* | (2006.01) |
| *A61K 31/401* | (2006.01) |
| *A61K 31/4152* | (2006.01) |
| *A61K 31/496* | (2006.01) |

(52) U.S. Cl.
CPC .......... *A61K 31/506* (2013.01); *A61K 31/404* (2013.01); *A61K 31/4418* (2013.01); *A61K 31/4439* (2013.01); *A61K 31/47* (2013.01); *A61K 45/06* (2013.01); *A61P 7/00* (2018.01); *A61P 35/00* (2018.01); *A61P 35/02* (2018.01); *A61K 31/401* (2013.01); *A61K 31/4152* (2013.01); *A61K 31/496* (2013.01)

(58) Field of Classification Search
CPC ............................ A61K 31/47; A61K 31/4439
USPC ............................................. 514/253.05, 269
See application file for complete search history.

(56) References Cited

U.S. PATENT DOCUMENTS

| | | | |
|---|---|---|---|
| 2011/0230457 A1* | 9/2011 | Berghausen ............ | A61P 35/00 514/210.02 |
| 2013/0245089 A1 | 9/2013 | Glenn et al. | |
| 2014/0011798 A1* | 1/2014 | Furet .................. | A61K 31/5377 514/210.18 |
| 2014/0148494 A1* | 5/2014 | Wang .................. | C07D 487/10 514/409 |
| 2014/0323482 A1* | 10/2014 | Ma .......................... | A61P 35/00 514/235.2 |
| 2017/0196866 A1* | 7/2017 | Ferretti .............. | A61K 31/4178 |

FOREIGN PATENT DOCUMENTS

| | | |
|---|---|---|
| WO | 2015198266 A1 | 12/2015 |
| WO | 2018/092020 A1 | 5/2018 |
| WO | 2018/178925 A1 | 10/2018 |

OTHER PUBLICATIONS

Iancu-Rubin et al. "Activation of p53 by MDM2 inhibitor RG7112 impair thrombopoiesis," Experimental Hematology, 2014, vol. 42, pp. 137-145 (Year: 2014).*

B. Higgins et al., "Preclinical Optimization of MDM2 Antagonist Scheduling for Cancer Treatment by Using a Model-Based Approach", Clinical Cancer Research, 2014, 3742-3752.

Hyman, D. et al.: "Dose- and regimen-finding phase I study of NVP-HDM201 in patients (pts) with TP53 wild-type (wt) advanced tumors", European Journal of Cancer, vol. 69, Dec. 1, 2016, abstract.

Hyman, D. M. et al.: Dose- and Regimen-finding Phase I Study of NVP-HDM201 in Patients With TP53 Wild-type Advanced Tumors, Dec. 2, 2016, Retrieved from the Internet: URL:http://www.poster-submission.com/ena2016/visitors/eposter/33139, the whole document.

Anonymous: "History of Changes for Study: NCT03940352 HDM201 in Combination With MBG453 or Venetoclax in Patients With Acute Myeloid Leukemia (AML) or High-risk M Syndrome (MDS)", Clinicaltrials.gov archive, Oct. 15, 2019, pp. 1-5.

Davidson-Moncada, J. et al.: "Dissecting the Immune Landscape of Acute Myeloid Leukemia", Biomedicines, vol. 6, No. 4, Nov. 25, 2018, p. 110.

* cited by examiner

*Primary Examiner* — Shengjun Wang
(74) *Attorney, Agent, or Firm* — David K. Cheung

(57) ABSTRACT

The present invention relates to HDM2-p53 interaction inhibitors for use in the treatment of cancer, wherein the drug is administered by a high dose intermittent dosing regimen. The present invention relates in particular to the HDM2-p53 interaction inhibitor HDM20I and the dosing regimen di, d8 of a 4 week cycle.

20 Claims, 4 Drawing Sheets

DOSE AND REGIMEN FOR HDM2-P53 INTERACTION INHIBITORS

FIELD OF THE INVENTION

The present invention relates to HDM2-p53 interaction inhibitors for use in the treatment of cancer, wherein the drug is administered following a high dose intermittent dosing regimen.

BACKGROUND OF THE INVENTION p53 is induced and activated by a number of potentially tumorigenic processes—including aberrant growth signals, DNA damage, ultraviolet light, and protein kinase inhibitors (Millard M, et al. *Curr Pharm Design* 2011; 17:536-559)—and regulates genes controlling cell growth arrest, DNA repair, apoptosis, and angiogenesis (Bullock A N & Fersht A R. Nat Rev Cancer 2001; 1:68-76; Vogelstein B, et al. Nature Education 2010; 3(9):6).

Human Double Minute-2 (HDM2) is one of the most important regulators of p53. It binds directly to p53, inhibiting its transactivation, and subsequently directing it towards cytoplasmic degradation (Zhang Y, et al. *Nucleic Acids Res* 2010; 38:6544-6554).

p53 is one of the most frequently inactivated proteins in human cancer, either through direct mutation of the TP53 gene (found in approximately 50% of all human cancers) (Vogelstein, B et al. Nature 2000; 408:307-310) or via suppressive mechanisms such as overexpression of HDM2 (Zhao Y, et al. *BioDiscovery* 2013; 8:4).

Potent and selective inhibitors of the HDM2-p53 interaction (also referred to as HDM2 inhibitors or MDM2 inhibitors), e.g. NVP-HDM201, have been shown to restore p53 function in preclinical cell and in vivo models (Holzer P, et al. Poster presented at AACR 2016, Abstract #4855).

Different dosing regimens were described for HDM2 inhibitors and tested in clinical studies. E.g. US2013/0245089 discloses a method of treating a patient suffering from cancer by administering to the patient 4-{[(2R,3S,4R,5S)-4-(4-Chloro-2-fluoro-phenyl)-3-(3-chloro-2-fluoro-phenyl)-4-cyano-5-(2, 2-dimethyl-propyl)-pyrrolidine-2-carbonyl]-amino}-3-methoxy-benzoic acid in an amount of from about 800 to about 3000 mg/day for an administration period of up to about 7 days, on days 1-7, of a 28 day treatment cycle, followed by a rest period of from about 21 to about 23 days.

A paper in Clinical Cancer Research by B. Higgins et al. (May 2014) disclosed a 28 days cycle schedule, where RG7388 is administered once weekly three times followed by 13 days of rest (28 days cycle schedule), or where the drug is administered for 5 consecutive days of a 28 days schedule. Further dosing regimens for HDM2 inhibitors are disclosed in WO 2015/198266.

HDM2 inhibitors and how to prepare them were disclosed for example in WO2013/111105 or WO2011/076786.

SUMMARY OF THE INVENTION

One of the objectives in the development of HDM2 inhibitor drugs is to find a dosing regimen which allows the administration of a high dose which ensures efficacy but at the same time reduces the risk of the occurrence of adverse events.

It has been surprisingly found that one type of dosing regimen is particularly useful for the treatment of solid tumors with HDM2 inhibitors. This dosing regimen was also found useful for the treatment of hematological tumors with MDM2 inhibitors.

Specifically, the present invention provides the following aspects, advantageous features and specific embodiments, respectively alone or in combination, as listed in the following items:

1. An HDM2-p53 interaction inhibitor for use in the treatment of cancer,
   wherein the drug is administered on two different administration days within a treatment cycle,
   wherein the first administration day and second administration day are interrupted by a short administration-free period, and the second administration day of the first or earlier treatment cycle and the first administration of the following cycle are interrupted by a long administration-free period,
   wherein the short administration-free period is composed of from 4 to 8 days, and the long administration-free period is composed of from 13 to 27 days, and
   wherein the treatment is composed of at least 2 treatment cycles.
2. The HDM2-p53 interaction inhibitor for use in the treatment of cancer according to item 1, wherein the short administration-free period is composed of from 4 to 8 days, and the long administration-free period is composed of from 18 to 22 days.
3. The HDM2-p53 interaction inhibitor for use in the treatment of cancer according to item 1, wherein the short administration-free period is composed of from 5 to 7 days, and the long administration-free period is composed of from 19 to 21 days.
4. The HDM2-p53 interaction inhibitor for use in the treatment of cancer according to item 1, wherein the short administration-free period is composed of 6 days, and the long administration-free period is composed of from 20 days.
5. The HDM2-p53 interaction inhibitor for use in the treatment of cancer according to any one of items 1 to 4, wherein said inhibitor is selected from the group of idasanutlin (RG7388, RO5503781), RG7775 (RO6839921), AMG232, DS3032 (DS3032b), ALRN-6924, ATSP-7041, CGM097, and HDM201.
6. The HDM2-p53 interaction inhibitor for use in the treatment of cancer according to any one of items 1 to 4, wherein said inhibitor is selected from the group of CGM097 and HDM201.
7. The HDM2-p53 interaction inhibitor for use in the treatment of cancer according to any one of items 1 to 4, wherein said inhibitor is CGM097.
8. The HDM2-p53 interaction inhibitor for use in the treatment of cancer according to any one of items 1 to 4, wherein said inhibitor is HDM201.
9. The HDM2-p53 interaction inhibitor for use in the treatment of cancer according to item 7, wherein said inhibitor is CGM097 sulfate.
10. The HDM2-p53 interaction inhibitor for use in the treatment of cancer according to items 8, wherein said inhibitor is HDM201 succinic acid.
11. The HDM2-p53 interaction inhibitor for use in the treatment of cancer according to items 8 or 10, wherein the daily dose on the administration days is from 100 mg to 200 mg.
12. The HDM2-p53 interaction inhibitor for use in the treatment of cancer according to items 8 or 10, wherein the daily dose on the administration days is from 100 mg to 150 mg.

13. The HDM2-p53 interaction inhibitor for use in the treatment of cancer according to items 8 or 10, wherein the daily dose on the administration days is 120 mg.
14. The HDM2-p53 interaction inhibitor for use in the treatment of cancer according to any one of the preceeding items, wherein the cancer is a TP53 wild-type tumor.
15. The HDM2-p53 interaction inhibitor for use in the treatment of cancer according to any one of the preceeding items, wherein the cancer is a solid tumor.
16. The HDM2-p53 interaction inhibitor for use in the treatment of cancer according to item 15, wherein the solid tumor is selected from sarcomas, e.g. liposarcoma or soft tissue sarcoma, melanomas, e.g. skin melanoma or uveal melanoma, blastomas (e.g. neuroblastoma), colon tumor, colorectal tumor, kidney tumor, and liver tumor.
17. The HDM2-p53 interaction inhibitor in combination with a thrombopoietin receptor agonist for use in the treatment of cancer according to any one of the preceeding items.
18. The HDM2-p53 interaction inhibitor in combination with a thrombopoietin receptor agonist for use in the treatment of cancer according to item 17, wherein the thrombopoietin receptor agonist is eltrombopag.
19. The HDM2-p53 interaction inhibitor for use in the treatment of cancer according to any one of the preceeding items, wherein the treatment reduces the risk of hematological toxicities.
20. The HDM2-p53 interaction inhibitor for use in the treatment of cancer according to item 19, wherein the hematological toxicities are selected from the group of thrombocytopenia, neutropenia, leucopenia, lymphopenia, anemia.
21. The HDM2-p53 interaction inhibitor for use in the treatment of cancer according to item 19, wherein the hematological toxicity is thrombocytopenia.
22. The HDM2-p53 interaction inhibitor for use in the treatment of cancer according to any one of the items 1-14, wherein the cancer is a hematological tumor.
23. The HDM2-p53 interaction inhibitor for use in the treatment of cancer according to item 22, wherein the hematological tumor is a leukemia.
24. The HDM2-p53 interaction inhibitor for use in the treatment of cancer according to item 22, wherein the hematological tumor is selected from acute myeloid leukemia (AML), myelodysplastic syndrome (MDS), and acute lymphoblastic leukemia (ALL).
25. The HDM2-p53 interaction inhibitor for use in the treatment of cancer according to any one of item 22 to 24, wherein the hematological tumor is a relapsed/refractory hematological tumor.
26. The HDM2-p53 interaction inhibitor for use in the treatment of cancer according to any one of the items 1-4, wherein the inhibitor is CGM097 or HDM201, preferably HDM201, wherein the daily dose on the administration days is from 100 mg to 150 mg, preferably 120 mg, and wherein the cancer is a relapsed/refractory TP53 wild-type hematological tumors selected from acute myeloid leukemia (AML), myelodysplastic syndrome (MDS), and acute lymphoblastic leukemia (ALL), preferably AML.

A preferred embodiment of the present invention is:

The HDM2-p53 interaction inhibitor drug HDM201 for use in the treatment of solid tumors, wherein the drug is administered on day 1 and day 8 of a 4 week (28 day) treatment cycle, wherein the treatment is composed of at least 2 treatment cycles, and the dose of the drug on each administration day is about 120 mg.

Another preferred embodiment of the present invention is:

The HDM2-p53 interaction inhibitor drug HDM201 for use in the treatment of hematological tumors, wherein the drug is administered on day 1 and day 8 of a 4 week (28 day) treatment cycle, wherein the treatment is composed of at least 2 treatment cycles, and the dose of the drug on each administration day is about 120 mg.

The dosing regimens of the present invention as described above provide a highly favorable therapeutic index, low incidence of grade 3/4 thrombocytopenia while achieving therapeutically relevant exposures, p53 pathway activation (GDF-15 upregulation), and clinical activity.

BRIEF DESCRIPTION OF THE DRAWINGS

In the following the present invention is described in detail with reference to accompanying figures in which.

Line at 120 ng/mL=95% tumor regression from human SJSA-1 xenograft rat. Line at 41 ng/mL=Average concentration for tumor stasis derived from TGI PK/PD modelling in human SJSA-1 (osteosarcoma) xenograft rat. Line at 19 ng/mL=Average concentration for tumor stasis derived from TGI PK/PD modelling in human HSAX2655 (liposarcoma) PDX rat. Calculation of average dose level (mg/day):

| Regimen | Daily dose (mg) | No. of administration days | Total dose per cycle (mg) | Cycle duration (days) | Average dose (mg/day) |
|---|---|---|---|---|---|
| 1A | 250 | 1 | 250 | 21 | 11.9 |
|  | 350 | 1 | 350 | 21 | 16.7 |
|  | 400 | 1 | 400 | 21 | 19 |

| Regimen | Daily dose (mg) | No. of administration days | Total dose per cycle (mg) | Cycle duration (days) | Average dose (mg/day) |
|---|---|---|---|---|---|
| 1B | 150 | 2 | 300 | 28 | 10.7 |
| 2A | 20 | 14 | 280 | 28 | 10 |
|  | 30 | 14 | 420 | 28 | 15 |
| 2C | 45 | 7 | 315 | 28 | 11.3 |

Figure 8:
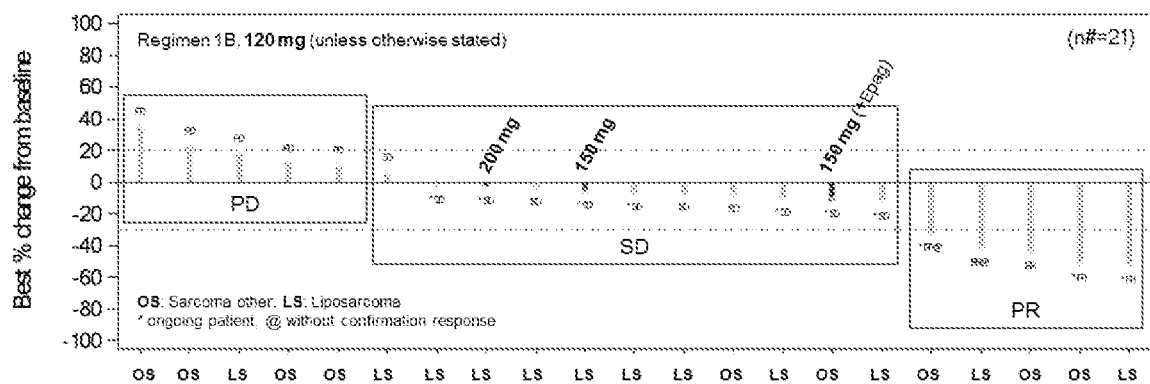

FIG. 8 shows the best percentage change from baseline in sum of diameter and best overall response for sarcoma (liposarcoma and other sarcomas) patients treated with HDM201 according to regimen 1B (September 2017). PD: progressing disease, SD: stable disease, PR: partial response.

DETAILED DESCRIPTION OF THE INVENTION

Herein after, the present invention is described in further detail and is exemplified.

In one aspect the invention provides:

An HDM2-p53 interaction inhibitor for use in the treatment of cancer,
  wherein the drug is administered on two different administration days within a treatment cycle,
  wherein the first administration day and second administration day are interrupted by a short administration-free period, and the second administration day of the first or earlier treatment cycle and the first administration of the following cycle are interrupted by a long administration-free period,
  wherein the short administration-free period is composed of from 4 to 8 days, and the long administration-free period is composed of from 13 to 27 days, and
wherein the treatment is composed of at least 2 treatment cycles.

"Administration day" means that this is a day on which the patient takes the HDM2 inhibitor drug. The patient may take the drug then as one single dose on that day or the daily dose is split up into smaller portions, e.g. in the morning one half of the daily dose and in the evening the other half. Preferably the dose is taken as one single dose.

"Administration-free days" are those days during which the patient is not receiving the HDM2 inhibitor drug. A series of administration-free days directly one after the other, not interrupted by a administration day, forms an "administration-free period." The patient may receive other drugs on an administration-free day. Therefore, administration-free means just free of the administration of an HDM2 inhibitor drug.

"Period is composed of from x to y days" means that the duration of said period is from x to y days long. E.g. the "period composed of 6 days" is a 6 days long time period.

With "administered on two different administration days within a treatment cycle" it is meant that there are only two administration days per treatment cycle, and not e.g. three or more administration day, neither only one administration days. In other words, the treatment cycle consists of two different administration days. "Two different administration days" means that the two days do not fall together to one administration day but are two separate, individual days, e.g. day 1 and day 8 of an 28 day treatment cycle.

The term "treatment cycle" indicates the number and order of days which form one treatment scheme with administration days and administration-free days before this treatment scheme is then repeated again. E.g. a treatment cycle of 28 days with administration days 1 and 8, means that the drug is administered on day 1, day 8, day 29, day 36, day 57, day 64, day 85 day 92, etc.

The present invention provides an HDM2-p53 interaction inhibitor drug, or any pharmaceutically acceptable salt thereof, for use in the treatment of cancer,
  wherein the drug is administered on two different administration days within a treatment cycle,
  wherein the first administration day and second administration day are interrupted by a short administration-free period, and the second administration day of the first or earlier treatment cycle and the first administration of the following cycle are interrupted by a long administration-free period,
  wherein the short administration-free period is composed of from 4 to 8 days, and the long administration-free period is composed of from 13 to 27 days, and
  wherein the treatment is composed of at least 2 treatment cycles.

Alternatively, the present invention provides a method for the treatment of cancer in human patients in need of such treatment which comprises administering an effective amount of an HDM2-p53 interaction inhibitor drug, or any pharmaceutically acceptable salt thereof,
  wherein said treatment is characterized in that the drug is administered on two different administration days within a treatment cycle,
  and the first administration day and second administration day are interrupted by a short administration-free period, and the second administration day of the first or earlier treatment cycle and the first administration of the following cycle are interrupted by a long administration-free period,
  and the short administration-free period is composed of from 4 to 8 days, and the long administration-free period is composed of from 13 to 27 days, and
  the treatment is composed of at least 2 treatment cycles.

As a further alternative the present invention provides the use of an HDM2-p53 interaction inhibitor drug, or any pharmaceutically acceptable salt thereof, for the preparation of a medicament for the treatment of cancer,
  characterized in that the drug is administered on two different administration days within a treatment cycle,
  and the first administration day and second administration day are interrupted by a short administration-free period, and the second administration day of the first or earlier treatment cycle and the first administration of the following cycle are interrupted by a long administration-free period,
  and the short administration-free period is composed of from 4 to 8 days, and the long administration-free period is composed of from 13 to 27 days, and
  the treatment is composed of at least 2 treatment cycles.

As a further alternative the present invention provides a medicament for the treatment of cancer comprising an HDM2-p53 interaction inhibitor drug or any pharmaceutically acceptable salt thereof,
  characterized in that the drug is administered on two different administration days within a treatment cycle,
  and the first administration day and second administration day are interrupted by a short administration-free period, and the second administration day of the first or earlier treatment cycle and the first administration of the following cycle are interrupted by a long administration-free period, and the short administration-free period is composed of from 4 to 8 days, and the long administration-free period is composed of from 13 to 27 days, and the treatment is composed of at least 2 treatment cycles.

The treatment is repeated as long as clinically meaningful, i.e. tumor growth is at least reduced, or controlled, and the adverse events are tolerable. The treatment of the present invention is composed of at least 2 treatment cycles, preferably of from 2 to 20 treatment cycles. However, if clinically meaningful the therapy is continued beyond the 20$^{th}$ treatment cycle.

Figures 1, 2:
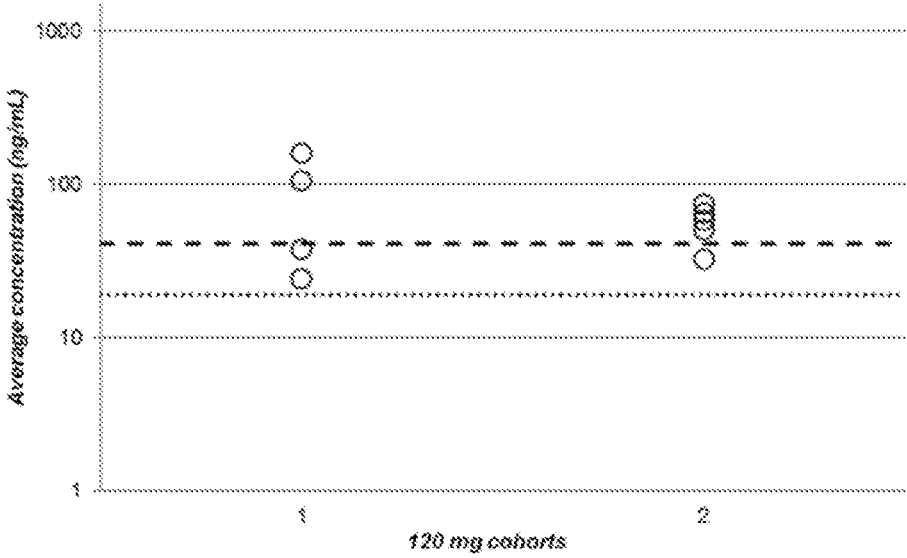
FIG. 1 illustrates the most preferred dosing regimen 1B (line "Pref.") of the present invention and some alternative regimens A1-E2. X1 and X2 are those days on which the HDM2 inhibitor drug is administered.
FIG. 2 shows the average concentration per cycle estimated for patients treated at 120 mg on regimen 1B. Cohort 1: 120 mg. cohort 2: 120 mg, new variant. Dashed line: Tumor stasis (SJSA-1 cell line), Dotted line: Tumor stasis (liposarcoma cell line). Each individual patient is represented by a circle.

FIG. 1 illustrates some specific dosing regimens which fall under the present invention. Line "Pref." provides the most preferred dosing regimen. The treatment cycle of said dosing regimen is composed of 4 weeks, i.e. 28 days (day 1-day 28). Administration days, indicated in that figure as "X1" (first administration day) and "X2" (second administration day) are on day 1 and day 8. That leaves an administration-free period of 6 days between X1 and X2, from day 2 to day 6 (short administration-free period) and an administration-free period of 20 days between X2 an X1 of the next treatment cycle from day 9 until day 28 (long administration-free period). Day 29 in this example would be then the day 1 of the next treatment cycle.

In the embodiments of the present invention, the doses on the administration days X1 and X2 are preferably the same, e.g. 120 mg at day 1 (X1) and 120 mg at day 8 (X2).

In the most preferred dosing regimen of the present invention, the treatment cycle lasts 28 days, i.e. 4 weeks, and the drug, the HDM2 inhibitor, is dosed on day 1 and day 8. This regimen is also referred to as "d1, d8 q4w" or by similar abbreviated versions. This most preferred dosing regimen is herein also referred to as "Regimen 1B".

Instead of the most preferred day 8 for the second administration day, that second administration day may alternatively be on day 6, 7, 9 or 10.

Depending on the length of the treatment cycle, preferably 3, 4, or 5 weeks, this leads to a shorter or longer administration-free periods. E.g. if the range of the length of the treatment cycle is from 3 to 5 weeks, the range for the short administration-free period is from 4 to 8 days, and the range of the long administration period is from 13 to 27 days. Most preferred is a treatment cycle of 4 weeks.

From all the possible regimens resulting from those ranges for the short and long administration-free periods as defined above, FIG. 1 shows the preferred options in lines A1, A2, B1, B2, C1, C2, C3, D1, D2, E1, E2. More preferable regimens are A2, B1, B2, C1, C2, C3, D1, D2, E1. Even more preferable are the regimens A2, B2, C2, D1, E1. Even more preferable are the regimens B2, C2, D1. Most preferable is regimen C2 which is equal to the "regimen 1B" as mentioned above.

The term "HDM2 inhibitor", also referred to as "HDM2i", "Hdm2i", "MDM2 inhibitor", "MDM2i", "Mdm2i", denotes herein any compound inhibiting the HDM-2/p53 or HDM-4/p53 interaction with an IC$_{50}$ of less than 10 µM, preferably less than 1 µM, preferably in the range of nM, measured by a Time Resolved Fluorescence Energy Transfer (TR-FRET) Assay. The inhibition of p53-Hdm2 and p53-Hdm4 interactions is measured by time resolved fluorescence energy transfer (TR-FRET). Fluorescence energy transfer (or Foerster resonance energy transfer) describes an energy transfer between donor and acceptor fluorescent molecules. For this assay, MDM2 protein (amino acids 2-188) and MDM4 protein (amino acids 2-185), tagged with a C-terminal Biotin moiety, are used in combination with a Europium labeled streptavidin (Perkin Elmer, Inc., Waltham, Mass., USA) serving as the donor fluorophore. The p53 derived, Cy5 labeled peptide Cy5-TFSDLWKLL (p53 aa18-26) is the energy acceptor. Upon excitation of the donor 10 molecule at 340 nm, binding interaction between MDM2 or MDM4 and the p53 peptide induces energy transfer and enhanced response at the acceptor emission wavelength at 665 nm. Disruption of the formation of the p53-MDM2 or p53-MDM4 complex due to an inhibitor molecule binding to the p53 binding site of MDM2 or MDM4 results in increased donor emission at 615 nm. The ratiometric FRET assay readout is calculated from the 15 raw data of the two distinct fluorescence signals measured in time resolved mode (countrate 665 nm/countrate 615 nm×1000). The assay can be performed according to the following procedure: The test is performed in white 1536w microtiterplates (Greiner Bio-One GmbH, Frickenhausen, Germany) in a total volume of 3.1 µl by combining 100 nl of compounds diluted in 90% DMSO/10% H2O (3.2% final DMSO concentration) with 2 µl Europium 20 labeled streptavidin (final concentration 2.5 nM) in reaction buffer (PBS, 125 mM NaCl, 0.001% Novexin (consists of carbohydrate polymers (Novexin polymers), designed to increase the solubility and stability of proteins; Novexin Ltd., ambridgeshire, United Kingdom), Gelatin 0.01%, 0.2% Pluronic (block copolymer from ethylenoxide and propyleneoxide, BASF, Ludwigshafen, Germany), 1 mM DTT), followed by the addition of 0.5 µl MDM2-Bio or MDM4-Bio diluted in assay buffer (final concentration 10 nM). Allow the solution to pre-incubate for 15 minutes at room temperature, followed by addition of 0.5 µl Cy5-p53 peptide in assay buffer (final concentration 20 nM). Incubate at room temperature for 10 minutes prior to reading the plate. For measurement of samples, an Analyst GT multimode microplate reader (Molecular Devices) with the following settings is used: Dichroic mirror 380 nm, Excitation 330 nm, Emission Donor 615 nm and Emission Acceptor 665 nm. IC50 values are calculated by curve fitting using XLfit. If not specified, reagents are purchased from Sigma Chemical Co, St. Louis, Mo., USA.

In the aspects of the invention, the HDM2 inhibitor may be selected from (S)-1-(4-Chloro-phenyl)-7-isopropoxy-6-methoxy-2-(4-{methyl-[4-(3-oxo-piperazin-1-yl)-trans-cyclohexylmethyl]-amino}-phenyl)-1,4-dihydro-2H-isoquinolin-3-one; (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one; (S)-1-(4-Chloro-phenyl)-7-isopropoxy-6-methoxy-2-(6-{methyl-[4-(4-methyl-3-oxo-piperazin-1-yl)-trans-cyclohexylmethyl]-amino}-pyridin-3-yl)-1,4-dihydro-2H-isoquinolin-3-one; (S)-1-(4-Chloro-phenyl)-7-isopropoxy-6-methoxy-2-(6-{methyl-[4-(3-methyl-4-oxo-imidazolidin-1-yl)-trans-cyclohexylmethyl]-amino}-pyridin-3-yl)-1,4-dihydro-2H-isoquinolin-3-one; (S)-1-(4-Chloro-phenyl)-7-isopropoxy-6-methoxy-2-(5-{methyl-[4-(3-methyl-4-oxo-imidazolidin-1-yl)-trans-cyclohexylmethyl]-amino}-pyrazin-2-yl)-1,4-dihydro-2H-isoquinolin-3-one; 1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one; (S)-5-(5-Chloro-1-methyl-2-oxo-1,2-dihydro-pyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one; 4-[(S)-5-(3-Chloro-2-fluoro-phenyl)-2-(2,4-dimethoxy-pyrimidin-5-yl)-3-isopropyl-6-oxo-3,4,5,6-tetrahydro-pyrrolo[3,4-d]imidazol-4-yl]-benzonitrile; (S)-5-(5-Chloro-2-oxo-1,2-dihydro-pyridin-3-yl)-6-(4-chloro-phenyl)-2-(2,4-dimethoxy-pyrimidin-5-yl)-

1-isopropyl-5,6-dihydro-1H-pyrrolo[3,4-d]imidazol-4-one;
(S)-5-(3-chloro-4-fluorophenyl)-6-(4-chlorophenyl)-2-(2,4-dimethoxypyrimidin-5-yl)-1-((R)-1-methoxypropan-2-yl)-5,6-dihydropyrrolo[3,4-d]imidazol-4(1H)-one;
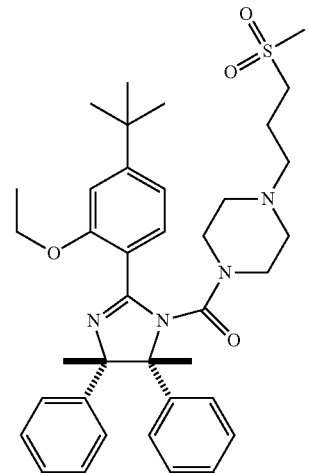
RG7112
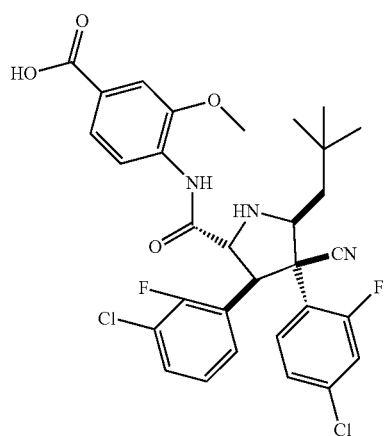
RG7388
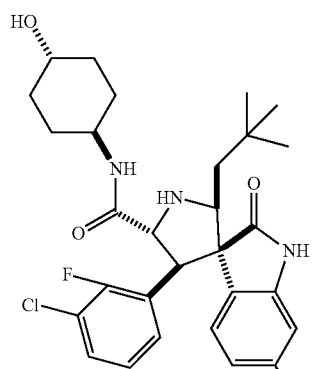
SAR299155
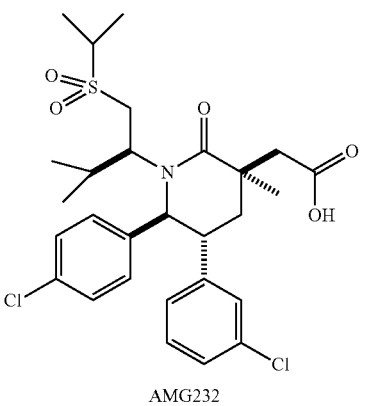
AMG232
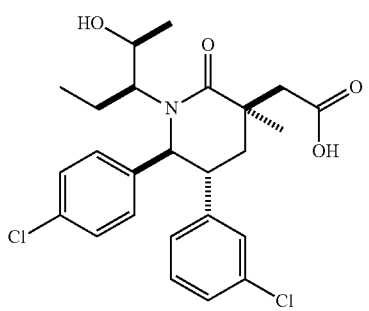
AM-8553
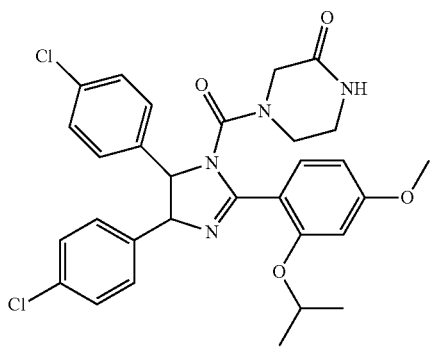
Nutlin-3
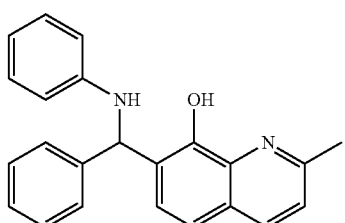
NSC 66811

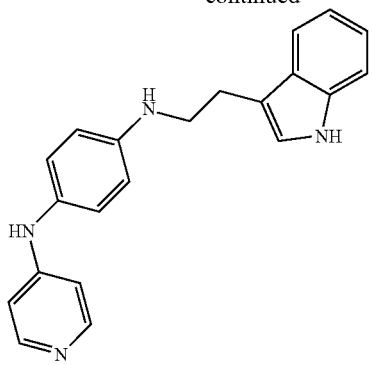

JNJ-26854165

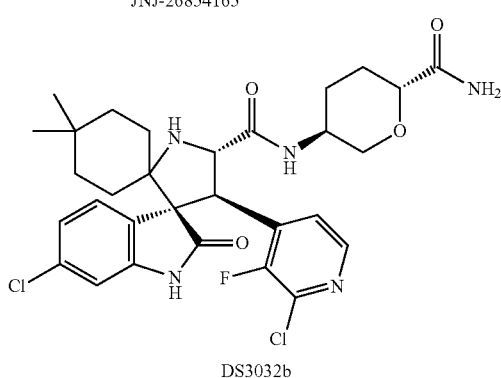

DS3032b and
(S)-5-(5-chloro-1-methyl-2-oxo-1,2-dihydropyridin-3-yl)-6-(4-chlorophenyl)-2-(2,4-dimethoxy-d6-pyrimidin-5-yl)-1-((R)-1-methoxypropan-2-yl)-5,6-dihydropyrrolo[3,4-d]imidazol-4(1H)-one; Idasanutlin (RG7388, RO5503781); RG7775 (RO6839921); AMG232; DS3032 (also referred to as DS3032b); ALRN-6924; ATSP-7041; CGM097; and HDM201.

Preferably the HDM2 inhibitor is selected from Idasanutlin (RG7388, RO5503781), RG7775 (RO6839921), AMG232, DS3032 (DS3032b), ALRN-6924, ATSP-7041, CGM097, and HDM201.

More preferably the HDM2 inhibitor is selected from HDM201, i.e. (S)-5-(5-Chloro-1-methyl-2-oxo-1,2-dihydropyridin-3-yl)-6-(4-chloro-phenyl)-2-(2,4-dimethoxy-pyrimidin-5-yl)-1-isopropyl-5,6-dihydro-1H-pyrrolo[3,4-d]imidazol-4-one, also referred to as (6S)-5-(5-Chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one,

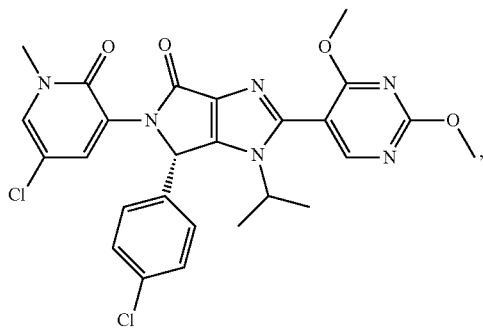 [SMILES: COc1ncc(-c2nc3c(n2C(C)C)[C@H](c2ccc(Cl)cc2)N(c2cc(Cl)cn(C)c2=O)C3=O)c(OC)n1]

and CGM097, i.e. (S)-1-(4-Chloro-phenyl)-7-isopropoxy-6-methoxy-2-(4-{methyl-[4-(4-methyl-3-oxo-piperazin-1-yl)-trans-cyclohexylmethyl]-amino}-phenyl)-1,4-dihydro-2H-isoquinolin-3-one, also referred to as trans-1(S)-(4-Chlorophenyl)-7-isopropoxy-6-methoxy-2-[4-[N-methyl-N-[4-(4-methyl-3-oxopiperazin-1-yl)cyclohexylmethyl]amino]phenyl]-1,2,3,4-tetrahydroisoquinolin-3-one,

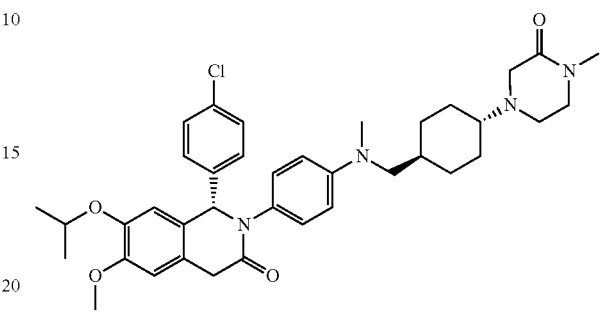

CGM097 may be present as free base or a pharmaceutically acceptable salt, preferably it is present as sulphate salt, more preferably as bisulphate salt. CGM097 salts are described in WO2012/066095.

HDM201 may be present as free molecule or as acid variant. The acid variant may be a salt formed of HDM201 with the acid, or a HDM201 acid complex, or as HDM201 acid co-crystal, preferably HDM201 is present as co-crystal. Preferable the acid is succinic acid. Most preferably, the HDM201 is present as succinic acid co-crystal. HDM201 variants are described in WO2013/111105.

Most preferably the HDM2 inhibitor is HDM201. The dosing regimens of the present invention are particularly well suited for the HDM201.

The dose on the two administration days of the dosing regimen of the present invention is particularly well suited for HDM201. For other HDM2 inhibitors this dose may need to be adapted initially based on the recommended total clinical dose per treatment cycle for those other HDM2 inhibitors divided by two. That initially adapted dose may then further adapted based on the observed clinical efficacy and toxicological findings with that initially adapted dose.

The daily dose of the HDM2 inhibitor on the administration days of the present invention may be from 50 mg to 400 mg, preferably from 80 mg to 300 mg, more preferably from 100 mg to 200 mg, even more preferably from 100 mg to 180 mg, even more preferably from 100 mg to 150 mg, even more preferably from 100 mg to 130 mg, even more preferably from 110 mg to 130 mg, most preferably about 120 mg. Those doses refer to the free drug molecule not taking into account any salt former, complex former or co-crystal former. Those daily doses are particularly suited for HDM201 as a HDM2 inhibitor.

In the embodiments of the present invention, the doses on the administration days X1 and X2 are preferably the same, e.g. 120 mg at day 1 (X1) and 120 mg at day 8 (X2).

Further, in the embodiments of the present invention, the doses on the administration days X1 and X2 are preferably single doses, taken by the patient as single dose units, e.g. 120 mg in one capsule or one tablet at day 1 (X1) and 120 mg in one capsule or one tablet at day 8 (X2).

The dosing regimens of the present invention are particularly well suited for solid tumors, particularly for TP53 wild-type solid tumors. Said solid tumors may be e.g. sarcomas, e.g. liposarcoma or soft tissue sarcoma, melanomas or osteosarcoma, melanomas, e.g. skin melanoma (cutaneous melanoma) or uveal melanoma, blastomas, e.g. neuroblastoma, colon tumor, colorectal tumor, kidney tumor (renal cell carcinoma), liver tumor (hepatic cell carcinoma), testicular cancer. The dosing regimens of the present invention are even more particularly well suited for sarcomas, e.g. liposarcomas and other sarcomas.

The dosing regimens of the present invention have the advantage that they reduces the risk of hematological toxicities, e.g. thrombocytopenia, neutropenia, leucopenia, lymphopenia, anemia. The dosing regimens of the present invention are particularly suited to reduce the risk of thrombocytopenia.

The treatment comprising the HDM2-p53 interaction inhibitors may be in combination with a thrombopoietin receptor agonist, preferably said thrombopoietin receptor agonist is eltrombopag (INN) which is available under the trademarks PROMACTA or REVOLADE. This combination may further reduce the risk of cytopenias, especially thrombocytopenia and/or neutropenia.

According to the present invention the daily dose on the administration days is from 100 mg to 150 mg. For example, the daily dose may be 100 mg, 105 mg, 110 mg, 120 mg, 125 mg, 130 mg, 135 mg, 140 mg, 145 mg or 150 mg. Preferably the daily dose is selected from 120 mg, 125 mg, 130 mg, 135 mg, 140 mg, 145 mg or 150 mg. More preferably the daily dose is selected from 120 mg or 150 mg. Even more preferably the daily dose is 120 mg.

As a further aspect of the present invention there is provided:

A combination of an HDM2-p53 interaction inhibitor with one or more other therapeutically active agents for use in the treatment of cancer,
  wherein the HDM2-p53 interaction inhibitor is administered on two different administration days within a treatment cycle,
  wherein the first administration day and second administration day are interrupted by a short administration-free period, and the second administration day of the first or earlier treatment cycle and the first administration of the following cycle are interrupted by a long administration-free period,
  wherein the short administration-free period is composed of from 4 to 8 days, and the long administration-free period is composed of from 13 to 27 days,
  wherein the treatment is composed of at least 2 treatment cycles.

The other therapeutically active agent is preferably an anti-cancer agent.

When treating hematological tumors (e.g. AML, MDS), said anti-cancer agent may be selected from
FLT3 inhibitors (e.g. gilteranib, quizartinib),
BCL2 inhibitors (e.g. navitoclax, venetoclax),
Other HDM2 inhibitors (e.g. idasanutlin)
hypomethylating agents (HMA) (e.g. Vidaza [azacytidine, 5-azacytidine], Dacogen [decitabine], guadecitabine),
anthracyclines (e.g. idarubicin, daunorubicin, doxorubicin, epirubicin);
anti-CD33 antibodies (e.g. Mylotarg [gemtuzumab], vadastuximab)
and other agents (e.g. AraC [cytarabine, aracytine])

When treating solid tumors (e.g. liposarcomas or other sarcomas, melanomas or uveal melanomas), said anti-cancer agent may be selected from
CDK-4/6 inhibitors (e.g. ribociclib, palbociclib),
Protein kinase C inhibitors (e.g. selinexor, one or more of the PKCi disclosed in WO2017/029588, i.e. 3-(1.H.-indol-3-yl)-4-[2-(4-methyl-piperazin-1-yl)-quinazolin-4-yl]-pyrrole-2,5-dione, or a pharmaceutically acceptable salt thereof or 3-amino-N-(3-(4-amino-4-methylpiperidin-1-yl)pyridin-2-yl)-6-(3-(trifluoromethylyl)pyrazine-2-carboxamide, or a pharmaceutically acceptable salt thereof, 3-amino-N-(3-(4-aminopiperidin-1-yl)pyridin-2-yl)-6-(3-(trifluoromethoxy)pyridin-2-yl)pyrazine-2-carboxamide, or a pharmaceutically acceptable salt thereof, and 3-amino-N-(3-(4-amino-4-methylpiperidin-1-yl)pyridin-2-yl)-6-(3-(trifluoromethoxy)pyridin-2-yl)pyrazine-2-carboxamide), and other agents (e.g. Halaven [eribulin], Yondelis [trabectedin]).

EXAMPLES

Example 1

This example provides a summary of the clinical safety and pharmacokinetic (PK) data that supports the dose and regimen of the present invention for single agent HDM201 for patients with solid tumors in the phase 1 trial CHDM201X2101.

Herein, data are disclosed from this multicenter, open-label, first-in-human Phase I study of HDM201 in patients with TP53 wild-type (WT) advanced solid tumors, progressing on standard therapy or for which no standard therapy exists (NCT02143635).

The preferred was found to be 120 mg HDM201 given on d1 and d8 of a 4 w cycle (regimen 1B). The data are from the monotherapy trial with a data cut-off date of 19 Sep. 2016.

The primary objective of the phase I part of the study is to determine the Maximum Tolerated Dose (MTD) and/or to identify the preferred dose of HDM201. The study design allowed parallel exploration of the safety, tolerability, and clinical activity of two broad dosing strategies for HDM201 across solid malignancies: intermittent high dose regimens (Regimen 1A and 1B) and extended low dose regimens (Regimen 2A and 2C). Table 1 summarizes the dosing regimens in each category that were evaluated in solid tumor patients. Table 2 provides the baseline characteristics of the patients involved in this study.

The endpoint for the primary objective is the incidence of Dose Limiting Toxicities (DLTs) during the first cycle of treatment. Although the primary analysis estimates the MTD based on DLT rate, the final preferred dose determination utilizes additional data beyond cycle 1 DLT rate, including later cycle tolerability, PK, PD and anti-tumor activity.

TABLE 1

HDM201 Dosing regimens and dose levels evaluated in solid tumor group

| | Dosing Regimen | Dose levels (number of patients) | Total number of patients |
|---|---|---|---|
| Intermittent high dose regimens | 1A (d1 Q3 weeks) | 12.5 mg (n = 1) 25 mg (n = 1) 50 mg (n = 4) 100 mg (n = 4) 200 mg (n = 5) 250 mg (n = 6) 350 mg (n = 5) | N = 26 |
| | 1B (d1, d8 of 4 w cycle) | 120 mg (n = 9) 150 mg (n = 8) 200 mg (n = 3) | N = 20 |

TABLE 1-continued

HDM201 Dosing regimens and dose levels evaluated in solid tumor group

| Dosing Regimen | | Dose levels (number of patients) | Total number of patients |
|---|---|---|---|
| Extended low dose regimens | 2A (2 weeks on/2 weeks off) | 1 mg (n = 1) | N = 20 |
| | | 2 mg (n = 2) | |
| | | 4 mg (n = 4) | |
| | | 7.5 mg (n = 4) | |
| | | 15 mg (n = 4) | |
| | | 20 mg (n = 5) | |
| | 2C (1 week on/3 weeks off) | 15 mg (n = 8) | N = 19 |
| | | 20 mg (n = 6) | |
| | | 25 mg (n = 5) | |

Patient Population

Patients involved in this study are characterized by the following criteria:

Patients aged ≥18 years with a locally advanced or metastatic solid malignancy that had progressed despite standard therapy, or for which no effective standard therapy exists Tumors with documented TP53 T status (minimum of no mutations in exons 5-8) obtained from a tumor biopsy collected no longer than 36 months before screening Measurable or non-measurable (but evaluable) disease as per Response Evaluation Criteria in Solid Tumors (RECIST) v1.1

Eastern Cooperative Oncology Group (ECOG) performance status 52

No prior treatment with compounds that inhibit the p53-HDM2 interaction, e.g. RG7388 or NVP-CGM097

No treatment with growth factors targeting the myeloid lineage, e.g. G-CSF, ≤2 weeks prior to study treatment Absolute neutrophil count>1,500/μL, platelet count>100,000/μL, hemoglobin>9.0 g/dL Table 2 provides the baseline characteristics of the patients involved in this study.

TABLE 2

Baseline characteristics (FAS)

| Characteristic | Regimen 1A (n = 26) | Regimen 1B (n = 20) | Regimen 2A (n = 20) | Regimen 2C (n = 19) | All Regimens (N = 85) |
|---|---|---|---|---|---|
| Age (median), years | 62 | 63 | 60 | 57 | 60 |
| Range | 18-80 | 31-78 | 38-76 | 37-74 | 18-80 |
| Sex (male), n (%) | 9 (35) | 11 (55) | 15 (75) | 13 (68) | 48 (56) |
| Race, n (%) | | | | | |
| Caucasian | 14 (54) | 14 (70) | 14 (70) | 15 (79) | 57 (67) |
| Black | 1 (4) | 0 | 0 | 0 | 1 (1) |
| Asian | 8 (31) | 5 (25) | 4 (20) | 4 (21) | 21 (25) |
| Other | 2 (8) | 1 (5) | 2 (10) | 0 | 5 (6) |
| Missing | 1 (4) | 0 | 0 | 0 | 1 (1) |
| WHO/ECOG PS* n (%) | | | | | |
| 0 | 12 (46) | 9 (45) | 11 (55) | 10 (53) | 42 (49) |
| 1 | 14 (54) | 11 (55) | 9 (45) | 9 (47) | 43 (51) |
| Tumor type, n (%) | | | | | |
| Liposarcoma | 3 (12) | 4 (20) | 1 (5) | 1 (5) | 9 (11) |
| Sarcoma (others) | 8 (31) | 2 (10) | 6 (30) | 3 (16) | 19 (22) |
| Skin melanoma | 0 | 1 (5) | 2 (10) | 0 | 3 (4) |
| Uveal melanoma | 2 (8) | 3 (15) | 1 (5) | 1 (5) | 7 (8) |
| Colon | 0 | 1 (5) | 4 (20) | 3 (16) | 8 (9) |
| Kidney | 0 | 0 | 1 (5) | 1 (5) | 2 (2) |
| Other | 13 (50) | 9 (45) | 5 (25) | 10 (53) | 37 (44) |
| Number of prior antineoplastic regimens, n (%) | | | | | |
| 0 | 0 | 2 (10) | 1 (5) | 1 (5) | 4 (5) |
| 1 | 7 (27) | 5 (25) | 1 (5) | 1 (5) | 14 (16) |
| 2 | 7 (27) | 4 (20) | 7 (35) | 5 (26) | 23 (27) |
| ≥3 | 12 (46) | 9 (45) | 11 (55) | 12 (63) | 44 (52) |

*WHO/ECOG PS: Eastern Cooperative Oncology Group/World Health Organization performance status Statistical Analyses Dose-escalation decisions were guided by the Bayesian logistic regression model (BLRM) with the escalation with overdose control principle (EWOC).

Decisions were based on a synthesis of data available from all dose levels and regimens evaluated in the study including dose-limiting toxicities, all Common Terminology Criteria for Adverse Events (CTCAE) Grade ≥2 toxicity data during the first cycle of treatment, and pharmacokinetic and pharmacodynamic data from evaluable patients.

Cycle 2 hematological toxicities were also taken into account for dose escalation and regimen selection.

Dose/Regimen Justification

Of the 4 dosing regimens evaluated in solid tumors with single agent HDM201, the intermittent high dose regimen 1B (d1 and d8 of 4 w cycle) were found to have the most favorable therapeutic index. Grade 3/4 thrombocytopenia was lowest in this regimen over all doses tested, and did not occur in patients treated at the selected RDE of 120 mg (see Table 3-1). The most frequent non-hematologic toxicities were gastrointestinal, but were not dose limiting at any of the dose levels evaluated across the 4 regimens. Pharmacokinetic data demonstrated that therapeutically relevant exposures were achieved at the 120 mg dose level for regimen 1B based on PK/PD modeling of preclinical data, and further supported by the observation of clinical efficacy in patients treated at this dose (1 patient with a long lasting PR, 1 patient with unconfirmed PR and 1 patient with SD). The 120 mg dose was also within the range of favorable doses recommended by the Bayesian logistic regression model (BLRM) supporting dose escalation. Therefore, regimen 1B at the dose of 120 mg was seen as most preferred dose and regimen.

Detailed Clinical Summary

At the time of data cut-off (19 Sep. 2016), 85 patients with solid tumors have been treated with HDM201 across the 4 dosing regimens evaluated (see Table 1). Dose limiting toxicities across all regimens evaluated were primarily related to myelosuppression.

Of all dose-limiting cytopenias, grade 3/4 neutropenia and thrombocytopenia were most commonly observed across the regimens (Table 3). Therefore, the comparative incidence of grade 3/4 cytopenias (most importantly thrombocytopenia) across the 4 regimens was a key factor informing the selection of regimen and dose for expansion.

It was found that during the study that HDM201-induced myelosuppression can have delayed onset (beyond cycle 1). Therefore, dose limiting hematologic toxicities occurring in cycle 2 were also factored into dose escalation decisions during the course of the study, using a non-binding sensitivity model. Table 4 summarizes the number of dose limiting toxicities during cycle 1 and dose limiting hematologic toxicities in cycle 2 across all the regimens evaluated in solid tumors.

Intermittent high dose regimen 1A and extended low dose regimen 2A were the first to be evaluated in dose escalation. Both regimens had unfavorable rates of DLT and delayed hematologic toxicities at dose levels achieving predicted therapeutically relevant exposures. Therefore, cohorts exploring two additional regimens were opened: intermittent high dose regimen 1B and extended low dose regimen 2C. In the regimen 2C, DLTs were observed at dose levels at which exposures were below those predicted to be efficacious based on PK/PD modeling.

Twenty patients have been treated according to regimen 1B at 3 different dose levels (120 mg, 150 mg and 200 mg). The most frequent AEs (all grades) reported as suspected due to study treatment in regimen 1B were nausea (12 patients, 60.0%), thrombocytopenia/platelet count decreased (9 patients, 45.0%), neutropenia/neutrophil count decreased (8 patients, 40.0%) and vomiting (5 patients, 25.0%). Nine patients (45.0%) of this group experienced at least one CTCAE grade 3/4 AE suspected to be treatment-related. The three most frequent CTCAE grade 3/4 AEs considered suspected to study treatment were: neutropenia/neutrophil count decreased (6 patients, 30.0%), lipase increase (3 patients, 15%) and thrombocytopenia/platelet count decrease (2 patients, 10.0%). One event of prolonged neutropenia (onset on day 22 and lasting 18 days) meeting DLT criteria was observed in one patient treated at the dose of 150 mg. See Table 5 for further details. Of the 4 regimens evaluated, regimen 1B had the lowest overall incidence of grade 3/4 thrombocytopenia (Table 3).

At the preferred dose of 120 mg (regimen 1B), there were no cases of grade 3/4 thrombocytopenia AEs (see Table 3-1). There were no dose interruptions or discontinuations due to thrombocytopenia at this dose level and no patients required platelet transfusions. The incidence of grade 3/4 neutropenia was similar across all regimens, and was observed in 2 out of 9 patients at the 120 mg dose level. There were no non-hematologic dose limiting toxicities or grade 3/4 AEs at this dose level.

Importantly, meaningful clinical activity was observed at the preferred dose of 120 mg (regimen 1B). Of 9 patients treated at this dose, there was 1 PR (lasting 18 weeks and still ongoing at the cutoff date) in a patient with soft tissue sarcoma, 1 unconfirmed PR and 1 SD (lasting 8 weeks) both in patients with liposarcoma, indicating that therapeutically relevant exposures are achieved at this dose and schedule.

TABLE 3

| | All cytopenia adverse events suspected to be study drug related-solid tumors | | | | | | | |
|---|---|---|---|---|---|---|---|---|
| | Neutropenia/ neutrophil count decreased* | | Leukopenia/white blood cell count decreased* | | Anemia | | Thrombocytopenia/ platelet count decreased* | |
| Regimen (n) | All Grades n (%) | G3/4 n (%) | All Grades n (%) | G3/4 n (%) | All Grades n (%) | G3/4 n (%) | All Grades n (%) | G3/4 n (%) |
| Regimen 1A (n = 26) | 9 (34.6) | 8 (30.7) | 9 (34.6) | 5 (19.2) | 10 (38.5) | 3 (11.5) | 12 (46.2) | 8 (30.8) |
| Regimen 1B (n = 20) | 8 (40.0) | 6 (30.0) | 5 (25.0) | 1 (5.0) | 5 (25.0) | 0 | 9 (45.0) | 2 (10.0) |
| Regimen 2A (n = 20) | 5 (25.0) | 4 (20.0) | 4 (20.0) | 3 (15.0) | 6 (30.0) | 4 (20.0) | 10 (50.0) | 7 (35.0) |

TABLE 3-continued

All cytopenia adverse events suspected to be study drug related-solid tumors

| Regimen (n) | Neutropenia/ neutrophil count decreased* | | Leukopenia/white blood cell count decreased* | | Anemia | | Thrombocytopenia/ platelet count decreased* | |
|---|---|---|---|---|---|---|---|---|
| | All Grades n (%) | G3/4 n (%) | All Grades n (%) | G3/4 n (%) | All Grades n (%) | G3/4 n (%) | All Grades n (%) | G3/4 n (%) |
| Regimen 2C (n = 19) | 3 (15.8) | 2 (10.5) | 2 (10.5) | 1 (5.3) | 4 (21.1) | 3 (15.8) | 8 (42.1) | 3 (15.8) |
| RDE (Regimen 1B 120 mg) (n = 9) | 2 (22.2) | 2 (22.2) | 3 (33.3) | 0 | 2 (22.2) | 0 | 4 (44.4) | 0 |

*includes combination of preferred terms

TABLE 4

Treatment cycle 1 DLTs and Cycle 2 hematologic dose limiting toxicities in solid tumors

| | Dosing Regimen | Dose levels (n) | DLTs (cycle 1) | Hematologic dose limiting toxicities (cycle 2) |
|---|---|---|---|---|
| Intermittent high dose regimens | 1A (d1 Q3 weeks) | 12.5 mg (n = 1) | 0 | 0 |
| | | 25 mg (n = 1) | 0 | 0 |
| | | 50 mg (n = 4) | 0 | 1 |
| | | 100 mg (n = 4) | 0 | 0 |
| | | 200 mg (n = 5) | 0 | 1 |
| | | 250 mg (n = 6) | 0 | 1 |
| | | 350 mg (n = 5) | 2 | 2 |
| | Total (%) | N = 26 | 2 (7.7%) | 5 (19.2%) |
| | 1B (d1, d8 of 4 w cycle) | 120 mg (n = 9) | 0 | 2 |
| | | 150 mg (n = 8) | 1 | 1 |
| | | 200 mg (n = 3) | 0 | Data not available at the clinical cutoff |
| | Total (%) | N = 20 | 1 (5%) | 3 (15%) |
| Extended low dose regimens | 2A (2 weeks on/2 weeks off) | 1 mg (n = 1) | 0 | 0 |
| | | 2 mg (n = 2) | 0 | 0 |
| | | 4 mg (n = 4) | 0 | 0 |
| | | 7.5 mg (n = 4) | 0 | 0 |
| | | 15 mg (n = 4) | 0 | 1 |
| | | 20 mg (n = 5) | 0 | 4 |
| | Total (%) | N = 20 | 0 (0%) | 5 (25%) |
| | 2C (1 week on/3 weeks off) | 15 mg (n = 8) | 0 | 1 |
| | | 20 mg (n = 6) | 0 | 0 |
| | | 25 mg (n = 5) | 2 | 0 |
| | Total (%) | N = 19 | 2 (10.5%) | 1 (5.3%) |

TABLE 5

All grades and grade 3/4 adverse events, suspected to be study drug related, by preferred term and treatment-solid tumors-Regimen 1B

| MEDDRA Preferred Term | HDM201 1B 120 mg N = 9 | | HDM201 1B 150 mg N = 8 | | HDM201 1B 200 mg N = 3 | | All subjects N = 20 | |
|---|---|---|---|---|---|---|---|---|
| | All Grades n (%) | Grade 3/4 n (%) | All Grades n (%) | Grade 3/4 n (%) | All Grades n (%) | Grade 3/4 n (%) | All Grades n (%) | Grade 3/4 n (%) |
| Total | 9 (100) | 4 (44.4) | 7 (87.5) | 4 (50.0) | 3 (100) | 1 (33.3) | 19 (95.0) | 9 (45.0) |
| Nausea | 7 (77.8) | 1 (11.1) | 4 (50.0) | 0 | 1 (33.3) | 0 | 12 (60.0) | 1 (5.0) |
| Neutropenia | 2 (22.2) | 2 (22.2) | 4 (50.0) | 3 (37.5) | 0 | 0 | 6 (30.0) | 5 (25.0) |
| Anaemia | 2 (22.2) | 0 | 2 (25.0) | 0 | 1 (33.3) | 0 | 5 (25.0) | 0 |
| Diarrhoea | 3 (33.3) | 0 | 2 (25.0) | 0 | 0 | 0 | 5 (25.0) | 0 |
| Thrombocytopenia | 1 (11.1) | 0 | 4 (50.0) | 2 (25.0) | 0 | 0 | 5 (25.0) | 2 (10.0) |
| Vomiting | 3 (33.3) | 0 | 2 (25.0) | 0 | 0 | 0 | 5 (25.0) | 0 |
| Decreased Appetite | 1 (11.1) | 0 | 3 (37.5) | 0 | 0 | 0 | 4 (20.0) | 0 |
| Fatigue | 1 (11.1) | 0 | 2 (25.0) | 1 (12.5) | 1 (33.3) | 0 | 4 (20.0) | 1 (5.0) |

TABLE 5-continued

All grades and grade 3/4 adverse events, suspected to be study drug related, by preferred term and treatment-solid tumors-Regimen 1B

| MEDDRA Preferred Term | HDM201 1B 120 mg N = 9 | | HDM201 1B 150 mg N = 8 | | HDM201 1B 200 mg N = 3 | | All subjects N = 20 | |
|---|---|---|---|---|---|---|---|---|
| | All Grades n (%) | Grade 3/4 n (%) | All Grades n (%) | Grade 3/4 n (%) | All Grades n (%) | Grade 3/4 n (%) | All Grades n (%) | Grade 3/4 n (%) |
| Lipase Increased | 1 (11.1) | 0 | 2 (25.0) | 2 (25.0) | 1 (33.3) | 1 (33.3) | 4 (20.0) | 3 (15.0) |
| Platelet Count Decreased | 3 (33.3) | 0 | 1 (12.5) | 0 | 0 | 0 | 4 (20.0) | 0 |
| Abdominal Pain | 1 (11.1) | 0 | 2 (25.0) | 0 | 0 | 0 | 3 (15.0) | 0 |
| Neutrophil Count Decreased | 0 | 0 | 3 (37.5) | 2 (25.0) | 0 | 0 | 3 (15.0) | 2 (10.0) |
| White Blood Cell Count Decreased | 2 (22.2) | 0 | 1 (12.5) | 0 | 0 | 0 | 3 (15.0) | 0 |
| Asthenia | 1 (11.1) | 0 | 1 (12.5) | 0 | 0 | 0 | 2 (10.0) | 0 |
| Blood Creatine Phosphokinase Increased | 2 (22.2) | 1 (11.1) | 0 | 0 | 0 | 0 | 2 (10.0) | 1 (5.0) |
| Blood Creatinine Increased | 1 (11.1) | 0 | 1 (12.5) | 0 | 0 | 0 | 2 (10.0) | 0 |
| Leukopenia | 1 (11.1) | 0 | 1 (12.5) | 1 (12.5) | 0 | 0 | 2 (10.0) | 1 (5.0) |
| Lymphopenia | 0 | 0 | 2 (25.0) | 1 (12.5) | 0 | 0 | 2 (10.0) | 1 (5.0) |
| Alanine Aminotransferase Increased | 0 | 0 | 1 (12.5) | 0 | 0 | 0 | 1 (5.0) | 0 |
| Alopecia | 1 (11.1) | 0 | 0 | 0 | 0 | 0 | 1 (5.0) | 0 |
| Amylase Increased | 0 | 0 | 0 | 0 | 1 (33.3) | 0 | 1 (5.0) | 0 |
| Blood Bilirubin Increased | 0 | 0 | 1 (12.5) | 0 | 0 | 0 | 1 (5.0) | 0 |
| Dehydration | 1 (11.1) | 0 | 0 | 0 | 0 | 0 | 1 (5.0) | 0 |
| Dry Skin | 1 (11.1) | 0 | 0 | 0 | 0 | 0 | 1 (5.0) | 0 |
| Dysgeusia | 1 (11.1) | 0 | 0 | 0 | 0 | 0 | 1 (5.0) | 0 |
| Eye Pain | 0 | 0 | 1 (12.5) | 0 | 0 | 0 | 1 (5.0) | 0 |
| Folliculitis | 0 | 0 | 1 (12.5) | 0 | 0 | 0 | 1 (5.0) | 0 |
| Gamma-Glutamyltransferase Increased | 0 | 0 | 1 (12.5) | 0 | 0 | 0 | 1 (5.0) | 0 |
| Headache | 0 | 0 | 1 (12.5) | 0 | 0 | 0 | 1 (5.0) | 0 |
| Hyperkalaemia | 1 (11.1) | 0 | 0 | 0 | 0 | 0 | 1 (5.0) | 0 |
| Hypocalcaemia | 1 (11.1) | 0 | 0 | 0 | 0 | 0 | 1 (5.0) | 0 |
| Influenza Like Illness | 0 | 0 | 1 (12.5) | 0 | 0 | 0 | 1 (5.0) | 0 |
| Lethargy | 0 | 0 | 1 (12.5) | 0 | 0 | 0 | 1 (5.0) | 0 |
| Monocytosis | 1 (11.1) | 0 | 0 | 0 | 0 | 0 | 1 (5.0) | 0 |
| Musculoskeletal Pain | 1 (11.1) | 0 | 0 | 0 | 0 | 0 | 1 (5.0) | 0 |
| Myalgia | 1 (11.1) | 0 | 0 | 0 | 0 | 0 | 1 (5.0) | 0 |
| Neuralgia | 0 | 0 | 1 (12.5) | 0 | 0 | 0 | 1 (5.0) | 0 |
| Oedema | 0 | 0 | 0 | 0 | 1 (33.3) | 0 | 1 (5.0) | 0 |
| Oral Candidiasis | 0 | 0 | 1 (12.5) | 0 | 0 | 0 | 1 (5.0) | 0 |
| Pruritus | 0 | 0 | 1 (12.5) | 0 | 0 | 0 | 1 (5.0) | 0 |
| Weight Decreased | 1 (11.1) | 0 | 0 | 0 | 0 | 0 | 1 (5.0) | 0 |

Preferred terms are sorted in descending frequency of <all grades> column, as reported in the <All subjects> column.
A subject with multiple occurrences of an AE under one treatment is counted only once in the AE category For that treatment.
A subject with multiple adverse events is counted only once in the total row.
Only AEs occurring during treatment or within 30 days of the last study medication are reported.

Safety

Dose-limiting toxicities, typically occurring during Cycle 2, were neutropenia and thrombocytopenia Study drug-related all grade adverse events (AEs; occurring in ≥10% of all patients) are presented in Table 6.

TABLE 6

Adverse Events Suspected To Be Study-drug Related, By Combined Treatment Regimens (All Grades, Occurring in ≥10%)

| | All Regimens (N = 85) | |
|---|---|---|
| Preferred Term, n (%) | All Grades | Grade 3/4 |
| Nausea | 44 (52) | 1 (1) |
| Thrombocytopenia | 27 (32) | 14 (16) |
| Anemia | 25 (29) | 10 (12) |
| Fatigue | 19 (22) | 2 (2) |
| Decreased appetite | 19 (22) | 2 (2) |
| Vomiting | 19 (22) | 0 |
| Neutropenia | 18 (21) | 15 (18) |
| Platelet count decreased | 15 (18) | 7 (8) |
| Diarrhea | 13 (15) | 0 |
| Leukopenia | 12 (14) | 8 (9) |
| White blood cell count decrease | 11 (13) | 3 (4) |

The most frequent non-hematologic toxicities were gastrointestinal, but were not dose-limiting at any of the dose levels evaluated across the 4 regimens; the most common all grade gastrointestinal AE was nausea (44/85; 52%), which was mostly mild to moderate in severity Study-drug related Grade 3/4 AEs of special interest are shown in Table 3. Grade 3/4 hematological toxicities suspected to be study-drug related were observed for all treatment regimens, occurring in up to ~35% of patients. Grade 3/4 thrombocytopenia was lowest in Regimen 1B.

Clinical PK

Pharmacokinetic data have been evaluated throughout the course of the dose escalation. Two HDM201 drug variants have been evaluated during the course of the study (refer to the protocol for further details). Non-compartmental PK analysis showed a median time to reach maximum plasma concentrations ranging from 2.0 to 5.8 h across the dose range (2 to 350 mg). A preliminary dose proportionality assessment showed approximately dose proportional PK (AUClast and Cmax) over the dose range studied. For the majority of dose cohorts, the inter-patient variability (CV % Geo-mean) for AUClast and Cmax was low to moderate (6 to 58.5%). Furthermore, an integrated analysis of all available HDM201 concentrations was conducted using a population approach. The PK of HDM201 was best described by a 1-compartment PK model with a delayed zero- and first-order absorption process, and a linear clearance. Body weight was identified as a statistically significant covariate on apparent central volume of distribution (Vc/F), in which Vc/F increased with increasing body weight.

To further support the preferred dose for HDM201, compartmental PK modeling was used to estimate the individual average concentration per cycle for the 9 patients treated at 120 mg on regimen 1B (FIG. 2). For the majority of patients (7 out of 9), the estimated average drug concentrations per cycle were near or above the most conservative average tumor stasis concentration of ≈41 ng/mL per cycle determined from PKPD modeling of preclinical data (human SJSA-1 xenograft rat model).

Figure 3:
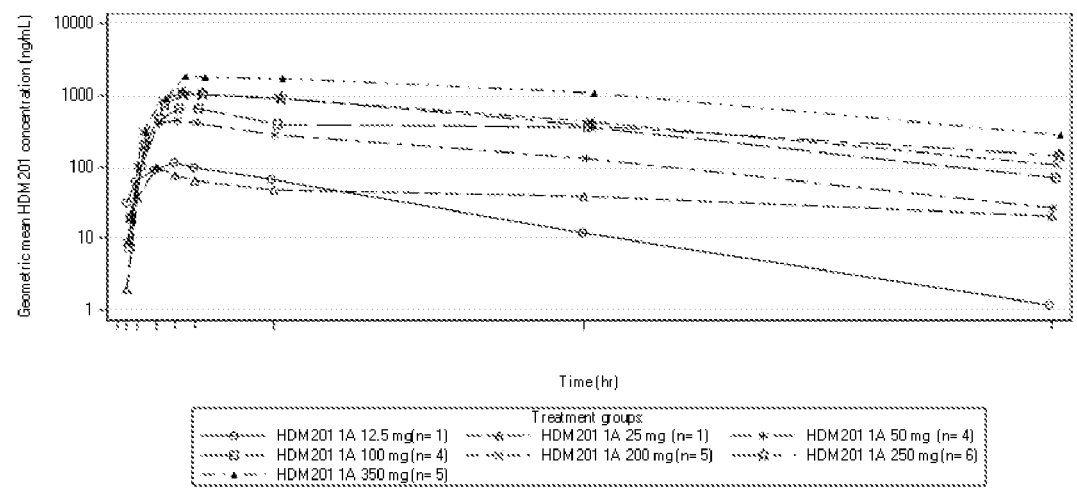
FIG. 3 shows the geometric mean concentration-time profile (Regimen 1A, Cycle 1 Day 1) (PAS).

Representative geometric mean plasma concentration-time profiles for NVP-HDM201 after single dose (Day 1) for treatment Regimen 1A (12.5-350 mg) are presented in FIG. 3 Oral absorption was fast (median Tmax 2-5.8 hours) and did not vary by dose group (2-350 mg)

Mean plasma exposures (AUClast and Cmax) increased with increasing dose, with no major deviations from dose proportionality after single and repeated doses NVP-HDM201 steady-state was generally reached by Day 8, with limited accumulation upon daily dosing Median half-life estimated after Day 1 single dose (50-350 mg) ranged from 13.7 to 23.1 h Inter-patient variability (CV % Geo-mean) in exposure was generally low to moderate. Compartmental population PK modeling of NVP-HDM201 was used to estimate the individual average plasma concentration for Cycle 1 and to allow comparison with preclinical average concentration for tumor stasis derived by PK/PD tumor growth modeling. The results are shown in FIG. 4.

Figure 4:
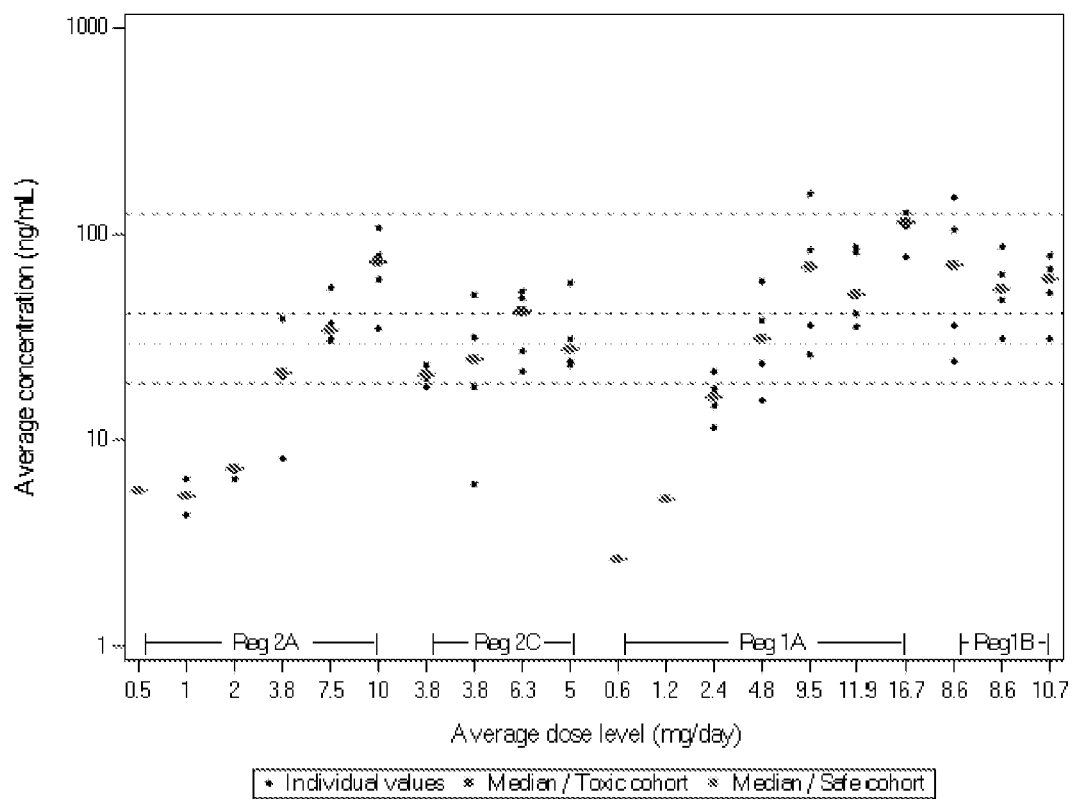
FIG. 4 shows the Individual human average NVP-HDM201 concentration during first cycle (DDS). Individual C (average)=individual AUC mode at the end of Cycle 1 divided by duration of Cycle 1 in hours. Average dose level=total cumulative dose at the end of Cycle 1 divided by the duration of Cycle 1 in days.

Compared with Regimen 2A/2C, the average plasma concentration reached with Regimen 1A/1B was closer to the predicted preclinical target efficacious levels (125 ng/mL) required for 95% tumor regression (upper dashed line in FIG. 5) and near or above the estimated average concentrations for the most conservative average tumor stasis concentration of =41 ng/mL (dashed line) determined from PK/PD modeling of human SJSA-1 xenograft rat model (FIG. 4).

The dashed line at concentration of =19 ng/mL represents average tumor stasis determined from PK/PD modeling of preclinical data from a liposarcoma (HSAX2655) patient-derived xenograft rat model.

The dashed line at concentration 29.4 ng/mL represents IC50 value determined from the cellular activity in SJSA-1 cell line.

Statistical Analysis

This study utilizes a Bayesian logistic regression model (BLRM) to support dose escalation and estimate the MTD and/or determine the preferred dose for HDM201. The BLRM with escalation with overdose control (EWOC) enables incorporation of available prior information and updates the model parameters based upon new information about observed dose limiting toxicities (DLT) seen in the clinical study. During the course of the dose escalation for regimen 1A and 1B, DLT incidence has been used to update the model and support the decision for the next dose. DLTs are defined as per Table 6-3 of the protocol and are events occurring during the first cycle treatment. When during the course of the study it became apparent that HDM201 induced bone marrow toxicity occurred predominantly during cycle 2, a non-binding sensitivity model including cycle 1 DLT and hematologic dose limiting AEs in cycle 2 (weighting all cytopenias equally) was used to guide dose escalation/RDE determinations. Additionally, decisions were at all times based on a synthesis of relevant data available from all dose levels evaluated in the study including low grade toxicities, PK, and PD data (when available) from evaluable patients.

The results of the BLRM using cycle 1 DLT events data from patients treated on regimen 1B (dose level 120 mg, 150 mg and 200 mg), supported escalation up to 400 mg HDM201. Median DLT rate at 120 mg was 3.5% and 25.7% as per protocol analysis and sensitivity analysis, respectively. Thus, 120 mg was found as preferred dose upon considering the lower incidence of clinically relevant grade 3/4 thrombocytopenia, manageable neutropenia, and the meaningful clinical activity observed at this dose.

Efficacy

At the time of data cut-off 2/46 (4%) patients receiving the high-dose intermittent regimens achieved PR (1 patient with STS-intimal sarcoma receiving Regimen 1A; 1 patient with STS-hemangiopericytoma receiving Regimen 1B) (Table 7). 15/46 (33%) patients receiving the high-dose intermittent regimens and 14/39 (36%) patients receiving the low-dose extended regimens achieved SD (Table 7).

While meaningful disease control was observed in all dosing regimens (DCR: 34%), PRs were only seen in Regimens 1A and 1B, suggesting that the high-dose intermittent regimens are more active.

By September 2017, strong antitumor efficacy had been observed for sarcoma patients (liposarcoma and other sarcomas). Out of 21 sarcoma patients treated with HDM201 according to regimen 1B, 5 patients showed partial response (PR), and 11 stable disease (SD). The disease only progressed (PD) in 5 patients (see FIG. 8).

TABLE 7

Best Overall Response (FAS) (November 2016)

| BOR, n (%) | Regimen 1A (n = 26) | Regimen 1B (n = 20) | Regimen 2A (n = 20) | Regimen 2C (n = 19) |
| --- | --- | --- | --- | --- |
| CR | 0 | 0 | 0 | 0 |
| PR | 1 (4) | 1 (5) | 0 | 0 |
| SD | 8 (31) | 7 (35) | 7 (35) | 7 (37) |
| PD | 14 (54) | 12 (60) | 12 (60) | 10 (53) |
| Unknown | 3 (12) | 0 | 1 (5) | 2 (11) |
| ORR | 1 (4) | 1 (5) | 0 | 0 |
| 95% CI | 0.1-19.6 | 0.1-24.9 | 0.0-16.8 | 0.0-17.6 |

TABLE 7-continued

Best Overall Response (FAS) (November 2016)

| BOR, n (%) | Regimen 1A (n = 26) | Regimen 1B (n = 20) | Regimen 2A (n = 20) | Regimen 2C (n = 19) |
|---|---|---|---|---|
| DCR | 9 (35) | 8 (40) | 7 (35) | 7 (37) |
| 95% CI | 17.2-55.7 | 19.1-63.9 | 15.4-59.2 | 16.3-61.6 |

BOR: best overall response;
CI, confidence interval;
CR: complete response;
DCR: disease control rate (CR or PR or SD);
FAS: full analysis set;
ORR: overall response rate (CR or PR);
PD: progressive disease;
PR: confirmed partial response;
SD: stable disease;
BOR is based on investigator's assessment of disease status using RECIST 1.1;
CR and PR are confirmed by repeat assessments performed not less than 4 weeks after the criteria for response is first met.
The 95% CI is calculated using the exact (Clopper-Pearson) interval.

The median relative dose intensity (RDI) for patients with at least stable disease or better at the end of 32 weeks of treatment was similar in low-dose extended Regimens 2A and 2C. Of the 2 high-dose intermittent regimens, Regimen 1B had a more favorable RDI, supporting its overall better tolerability at therapeutically relevant doses (Table 8).

TABLE 8

Relative Dose Intensity Summary For Patients With At Least Stable Disease At The End Of 32 Weeks Of Treatment (SAS)

| Relative dose intensity during the first 32 weeks of treatment | Regimen 1A (n = 20) | Regimen 1B (n = 20) | Regimen 2A (n = 13) | Regimen 2C (n = 19) |
|---|---|---|---|---|
| N | 11 (55) | 8 (40) | 7 (53.8) | 9 (47.4) |
| Median | 0.73 | 0.87 | 0.97 | 1 |
| Range | 0.33-1 | 0.5-1 | 0.72-1.42 | 0.61-1 |

SAS, safety analysis set.
n = total number of patients treated including only the treatment groups in the corresponding regimens:
Regimen 1A: ≥100 mg;
Regimen 1B: ≥120 mg;
Regimen 2A: ≥7.5 mg;
Regimen 2C: ≥15 mg
N = number of patients with at least one SD or PR or CR or patients discontinued treatment for reasons other than PD.

Example 2: Detailed Pharmacokinetical Data 5.1.2.1.1 Monotherapy in Adult Patients [HDM201X2101]

The PK of HDM201 have been evaluated in the ongoing single agent Phase I clinical trial in patients with solid tumors and hematological malignancies (HDM201X2101). Patients have been treated with a single dose on Day 1 in a three-week cycle (q3w, regimen 1A), with a single dose on Day 1 and Day 8 in a four-week cycle (d1 and d8 of 4 w cycle, regimen 1B), or with daily dosing for the first 7 or 14 days in a four-week cycle (regimen 2C [q.d., 1 w on/3 w off] or regimen 2A [q.d., 2 w on/2 w off], respectively). PK assessments were conducted following single dose and repeated administration. Preliminary PK parameters from non-compartmental analysis of plasma concentration-time profiles are summarized by dose regimen and tumor type (data cut-off 1 Apr. 2016). PK parameters for Regimen 2A (Day 1 and 14 of Cycle 1 for doses from 1 to 20 mg) and Regimen 1A (Day 1 of Cycle 1 for doses from 12.5 to 350 mg) in solid tumor patients are summarized as representative of the PK for daily and less frequent dosing regimens (Tables 9, 10 and 11).

TABLE 9

Summary of primary PK parameters for HDM201 daily regimen 2A after single dose (Solid malignancies)

Treatment (Day 1) AUClast (ng * hr/mL), Cmax (ng/mL), Tmax (hr)
HDM201 2A, 1 mg (N = 1) N = 1 N = 1 N = 1
    134.3 7.9 8.0
HDM201 2A, 2 mg (N = 2) N = 2 N = 2 N = 2
    169.1 (31.5) 12.0 (23.7) 3.4
HDM201 2A, 4 mg (N = 4) N = 4 N = 4 N = 4
    192.6 (29.1) 17.6 (22.8) 2.5
HDM201 2A, 7.5 mg (N = 4) N = 4 N = 4 N = 4
    598.1 (49.8) 39.0 (43.9) 5.8
HDM201 2A, 15 mg (N = 4) N = 4 N = 4 N = 4
    1301.6 (71.0) 91.5 (56.9) 3.1
HDM201 2A, 20 mg (N = 5) N = 5 N = 5 N = 5
    2300.9 (33.3) 163.6 (15.9) 2.0

Values are Geo Mean (% CV) except for Tmax where median is presented.
AUClast is calculated from 0-24 h

TABLE 10

Summary of primary PK parameters for HDM201 daily regimen 2A on day 14 (Solid malignancies)

Treatment (Day 14) AUClast (ng * hr/mL) Cmax (ng/mL) Tmax (hr)
HDM201 2A, 1 mg (N = 1) N = 1 N = 1 N = 1
    99.5 14.9 4.0
HDM201 2A, 2 mg (N = 2) N = 2 N = 2 N = 2
    109.3 (6.0) 17.5 (4.9) 3.9
HDM201 2A, 4 mg (N = 4) N = 3 N = 3 N = 3
    155.0 (21.7) 25.6 (23.9) 4.0
HDM201 2A, 7.5 mg (N = 4) N = 2 N = 2 N = 2
    221.7 (44.7) 36.1 (43.6) 3.9
HDM201 2A, 15 mg (N = 4) N = 4 N = 4 N = 4
    688.8 (29.2) 106.0 (27.9) 3.0
HDM201 2A, 20 mg (N = 5) N = 4 N = 4 N = 4
    1264.0 (26.3) 214.5 (21.4) 4.0

Values are Geo Mean (% CV) except for Tmax where median is presented.
AUClast is calculated from 0-24 h

TABLE 11

Summary of primary PK parameters for HDM201 q3w regimen 1A after single dose (Solid malignancies)

Treatment (Day 1) AUClast (ng * hr/mL) Cmax (ng/mL) T½ (hr) Tmax (hr)
HDM201 1A, 12.5 mg (N = 1) N = 1 N = 1 N = 1 N = 1
    1483.1 118.0 7.2 3.2
HDM201 1A, 25 mg (N = 1) N = 1 N = 1 N = 1 N = 1
    1773.6 100.0 31.1 2.1
HDM201 1A, 50 mg (N = 4) N = 4 N = 4 N = 4 N = 4
    8028.8 (25.6) 467.0 (13.0) 11.8 (27.9) 3.0
HDM201 1A, 100 mg (N = 4) N = 4 N = 4 N = 3 N = 4
    14287.0 (58.5) 663.3 (30.1) 16.3 (21.6) 3.5
HDM201 1A, 200 mg (N = 5) N = 5 N = 5 N = 4 N = 5
    26255.2 (56.2) 1168.8 (43.7) 15.1 (102.7) 3.0
HDM201 1A, 250 mg (N = 6) N = 6 N = 6 N = 5 N = 6
    23850.1 (38.5) 1072.6 (36.3) 15.3 (43.8) 3.5
HDM201 1A, 350 mg (N = 5) N = 5 N = 5 N = 4 N = 5
    50527.1 (24.3) 1936.4 (40.5) 15.1 (47.1) 4.1

Values are Geo Mean (% CV) except for Tmax where median is presented.
AUClast is calculated from 0-24 h Following oral dosing (HDM201 capsule, fasted), the median time to reach maximum plasma concentrations ranged from 2.0 to 5.8 h across the dose range (2 to 350 mg). With the daily dosing regimen, HDM201 steady-state was generally reached by Day 8, and accumulation was less than 2-fold. Mean T½ estimated after a single dose (50 to 350 mg) ranged from 11.8 to 16.3 h. A preliminary dose proportionality assessment showed approximately dose proportional PK (AUClast and Cmax) over the dose range studied on Day 1 single dose (1 to 350 mg) and after multiple doses on Day 14 (1 to 30 mg q.d.). For the majority of dose cohorts, the inter-patient variability (CV % Geo-mean) for AUClast and Cmax was low to moderate (6 to 58.5%).

Furthermore, the individual PK data was best described by a 1-compartment PK model with a delayed zero- and first-order absorption process (data cut-off 1 Apr. 2016). The mean population estimate for apparent oral clearance (CL/F) and apparent volume of distribution of the central compartment (Vc/F) were 6.18 L/h and 119 L respectively (relative standard error of 7%), with inter-individual variability of 48% (CL/F) and 30% (Vc/F). Body weight was identified as a statistically significant covariate on Vc/F.

Example 3: PK/PD Model of Thrombocytopenia

Figure 5:
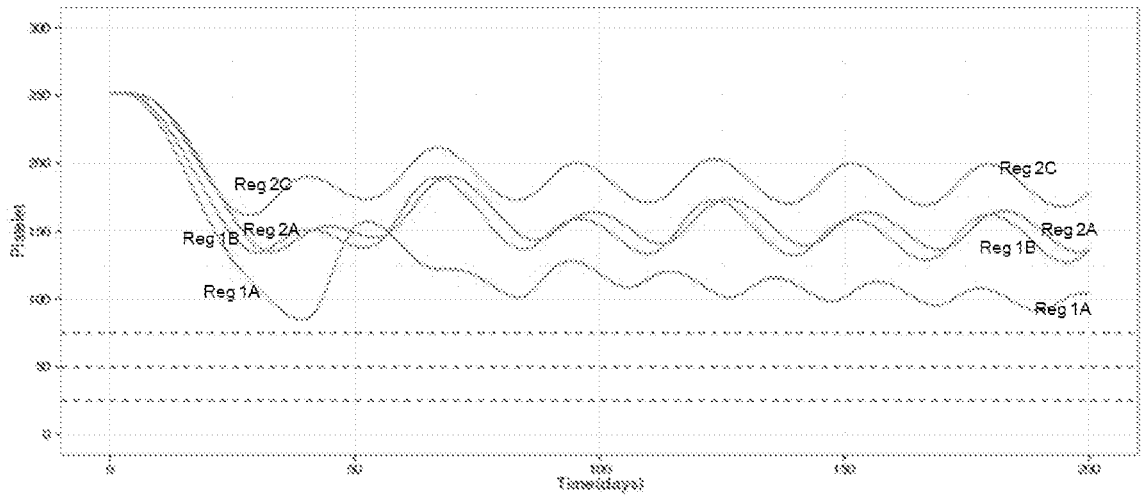
FIG. 5 shows the platelet kinetic profiles modeled based on the following doses as tested in each regimen (in order from top to bottom): Reg2C (D1-7 Q4wk): 25 mg (6.25 mg/d); Reg2A (D1-14 Q4wk): 20 mg (10 mg/d); Reg1B (Days 1, 8 Q4wk): 150 mg (10.7 mg/d); Reg1A (D1 Q3wk): 350 mg (16.7 mg/d).

Based on individual PK and platelet counts data overtime a PK/PD model was established.
PK model: 1 compartment with biphasic absorption.
PD model: Adjusted Friberg model for thrombocytopenia including PLT transfusions and effect on HDM201 on proliferative cells and regulations.
Data Base:
n=73 subjects
1301 PK observations
1023 PD platelets observations
427 PD GDF15 observations The platelet kinetic profiles shown in FIG. 5 are modeled based on the following doses as tested in each regimen (in order from top to bottom in FIG. 5):
Reg2C (D1-7 Q4wk): 25 mg ((25 mg×7 administration days)/28 days cycle=6.25 mg/day)
Reg2A (D1-14 Q4wk): 20 mg ((20 mg×14 administration days)/28 days cycle=10 mg/day)
Reg1B (Days 1, 8 Q4wk): 150 mg ((150 mg×2 admin. days)/28 days cycle=10.7 mg/day)
Reg1A (D1 Q3wk): 350 mg ((350 mg×1 administration day)/21 days cycle=16.7 mg/day)

Based on this modeling, 1B has best overall platelet kinetic profile of the regimens that have demonstrated single agent activity.

The first occurrence of G4 thrombocytopenia with regimen 1B 150 mg in the clinical study occurred only after 100 days.

Addition of Eltrombopag to 1B could mitigate the relative delay and decreased peak of platelet recovery with subsequent cycles.

Example 4: Drug Product

The drug product consists of HDM201 succinic acid drug substance filled directly into hard gelatin capsules (HGC), and does not contain any other excipients. The drug product is provided in four dosage strengths: 1 mg, 2.5 mg, 10 mg and 100 mg (based on the weight of the free form), intended for oral use. The 1 mg strength capsule is a "Size 3" yellow HGC, the 2.5 mg strength capsule is a "Size 3" Swedish Orange HGC, the 10 mg strength capsule is a "Size 1" Grey HGC, and the 100 mg is a "Size 0" Swedish Orange HGC. The drug product is packaged in child resistant, induction sealed High Density Polyethylene (HDPE) bottles.

Example 5: Regimen 1B for Hematological Tumors

This example provides a summary of the clinical data of the phase 1 trial CHDM201X2101 (data cut-off date of 7 Dec. 2016) that demonstrates that the dose regimen "1B", is also suitable for the treatment of patients with hematological tumors.

Herein, data are disclosed from this multicenter, open-label, first-in-human Phase I study of HDM201 in patients with advanced TP53 wild-type (WT) leukemias.

The clinical study design allowed parallel exploration of the safety, tolerability, and clinical activity (efficacy) of two broad dosing strategies for HDM201 during dose escalation: intermittent high dose regimens (Regimen 1A and 1B) and extended low dose regimens (Regimen 2A and 2C). Table 1 summarizes the dosing regimens in each category that were evaluated in patients with hematologic tumors.

TABLE 1

HDM201 Dosing regimens and dose levels evaluated in hematologic malignancies

| | Dosing Regimen | Dose levels (number of patients) | Total number of patients |
|---|---|---|---|
| Intermittent high dose regimens | 1A (d1 Q3W) | 250 mg (3) 350 mg (4) 400 mg (8AML; 1ALL) | 16 |
| | 1B (d1, d8 Q4W) | 150 mg (6) | 6 |
| Extended low dose regimens | 2A (2 week on/2 weeks off) | 20 mg (3) 30 mg (4) | 7 |
| | 2C (1 week on/3 weeks off) | 45 mg (7AML; 1 ALL) | 8 |

At the time of data cut-off, a total of 37 patients (35 AML and 2 ALL) have been treated with HDM201 across the 4 dosing regimens evaluated (refer to Table 1). In regimen 1B, 6 patients with AML have been treated with HDM201 with 150 mg dose on d1 and d8 of a 28 d treatment cycle.

Table 2 provides the characteristics of those patients.

TABLE 2

Patient characteristics

| | Reg 1A (n = 16) | Reg 1B (n = 6) | Reg 2A (n = 7) | Reg 2C (n = 8) |
|---|---|---|---|---|
| Median age, years (range) | 70 (23-81) | 71 (64-83) | 63 (26-72) | 75 (41-81) |
| Male, n (%) | 10 (63) | 1 (17) | 7 (100) | 7 (88) |
| ECOG PS, n (%) | | | | |
| 0 | 2 (13) | 0 (0) | 4 (57) | 0 (0) |
| 1 | 13 (81) | 5 (83) | 2 (29) | 7 (88) |
| 2 | 1 (6) | 1 (17) | 1 (14) | 1 (13) |

TABLE 2-continued

| Patient characteristics | | | | |
|---|---|---|---|---|
| | Reg 1A (n = 16) | Reg 1B (n = 6) | Reg 2A (n = 7) | Reg 2C (n = 8) |
| Disease history for AML patients | n = 15 | n = 6 | n = 7 | n = 7 |
| Median prior treatment regimens, n (range) | TBC | TBC | TBC | TBC |
| WHO classification at initial diagnosis, n (%) | | | | |
| AML (BM blasts >30%) | 8 (53) | 6 (100) | 6 (86) | 3 (43) |
| AML with multilineage dysplasia (BM blasts 21-30%) | 6 (40) | 0 (0) | 1 (14) | 4 (57) |
| Cytogenetics at initial diagnosis, n (%) | | | | |
| Favorable | 0 (0) | 0 (0) | 0 (0) | 0 (0) |
| Intermediate | 3 (20) | 2 (33) | 1 (14) | 2 (29) |
| Unfavorable | 3 (20) | 0 (0) | 1 (14) | 2 (29) |
| Unknown | 3 (20) | 2 (33) | 1 (14) | 0 (0) |
| Missing | 6 (40) | 2 (33) | 4 (57) | 3 (43) |
| Prior allogeneic stem cell transplant, n (%) | 2 (13) | 1 (17) | 1 (14) | 0 (0) |

The patient population is further characterized by the following inclusion criteria:
- Patient (male or female) ≥18 years of age.
- ECOG performance status 0-2.
- Relapsed/Refractory AML (both de novo or secondary AML) expect for Acute Promyelocytic Leukemia (APL) with t(15;17), or previously untreated patients who are considered inappropriate candidates for standard induction therapy
- In dose escalation only, high and very high risk MDS according to the revised International Prognostic Scoring System (IPSS-R) who have failed prior therapies, such as azacitidine and decitabine (Patients with IPSS-R score of >4.5).
- In dose escalation only, relapsed/Refractory Acute Lymphoblastic Leukemia (B-ALL or T-ALL) including Ph+ ALL, or previously untreated patients who are considered inappropriate candidates for standard induction therapy. Patients with Ph+ ALL who show early markers of relapse in MRD surveillance can be considered for inclusion as long as other therapies such as TKIs are exhausted or cannot be given.
- Tumor of the patient is TP53 wt characterized by, at a minimum, no mutations in exons 5, 6, 7 and 8, and the p53 status was obtained from a bone-marrow sample, collected no longer than 3 months before signing the main ICF.

Safety and Tolerability Profile of Regimen 1B in Hematological Tumors

Tables 3 and 4 provide safety and tolerability information about dosing regimen 1B in comparison with other intermittend high dose regimens and extended low dose regimens. For the regimen 1B only 1 dose limiting toxicity (DLT) were found. The occurrence of all grades and grade 3/4 adverse events were found to be comparatively low.

TABLE 3

| Cycle 1 DLTs in hematological tumors | | | |
|---|---|---|---|
| | Dosing Regimen | Dose levels (number of evaluable patients) | DLTs |
| Intermittent high dose regimens | 1A (d1 Q3W) | 250 mg (3) | 0 |
| | | 350 mg (4) | 0 |
| | | 400 mg (9) | 4 |
| | Total | N = 16 | 4: Infection G3, GVHd reactivation G3, Stomatitis G3 Hypophosphatemia G4 Subarachnoid hemorrhage (fatal) Hypophosphatemia G4 |
| | 1B (d1, d8 Q4W) | 150 mg (6) | 1 |
| | Total | N = 6 | 1: Acute Kidney Injury G4 |
| Extended low dose regimens | 2A (2 weeks on/2 weeks off) | 20 mg (3) | 0 |
| | | 30 mg (3) | 0 |
| | Total | N = 6 | 0 |
| | 2C (1 week on/3 weeks off) | 45 mg (8) | 1 |
| | Total | N = 8 | 1 - Tumor Lysis Syndrome G4 |

TABLE 4

All grades and grade 3/4 adverse events, suspected to be study drug related, by preferred term and regimens-hematological tumors

| MEDDRA Preferred Term | HDM201 Regimen 1A subjects N = 16 | | HDM201 Regimen 1B subjects N = 6 | | HDM201 Regimen 2A Subjects N = 7 | | HDM201 Regimen 2C subjects N = 8 | | All subjects N = 37 | |
|---|---|---|---|---|---|---|---|---|---|---|
| | All Grades n (%) | Grade 3/4 n (%) | All Grades n (%) | Grade 3/4 n (%) | All Grades n (%) | Grade 3/4 n (%) | All Grades n (%) | Grade 3/4 n (%) | All Grades n (%) | Grade 3/4 n (%) |
| Total | 15 (93.8) | 12 (75.0) | 5 (83.3) | 5 (83.3) | 5 (71.4) | 3 (42.9) | 8 (100) | 5 (62.5) | 33 (89.2) | 25 (67.6) |
| Nausea | 10 (62.5) | 0 | 4 (66.7) | 0 | 3 (42.9) | 0 | 3 (37.5) | 0 | 20 (54.1) | 0 |
| Thrombocytopenia/Platelet Count Decreased | 8 (50.0) | 8 (50.0) | 3 (50.0) | 3 (50.0) | 2 (28.6) | 2 (28.6) | 5 (62.5) | 5 (62.5) | 18 (48.6) | 18 (48.6) |
| Anaemia | 6 (37.5) | 4 (25.0) | 2 (33.3) | 2 (33.3) | 3 (42.9) | 2 (28.6) | 5 (62.5) | 3 (37.5) | 16 (43.2) | 11 (29.7) |
| Neutropenia/Neutrophil Count Decreased | 6 (37.5) | 6 (37.5) | 1 (16.7) | 1 (16.7) | 1 (14.3) | 1 (14.3) | 4 (50.0) | 3 (37.5) | 12 (32.4) | 11 (29.7) |
| Febrile Neutropenia | 4 (25.0) | 4 (25.0) | 2 (33.3) | 2 (33.3) | 2 (28.6) | 2 (28.6) | 3 (37.5) | 3 (37.5) | 11 (29.7) | 11 (29.7) |
| Decreased Appetite | 4 (25.0) | 0 | 1 (16.7) | 0 | 1 (14.3) | 0 | 4 (50.0) | 0 | 10 (27.0) | 0 |
| Tumour Lysis Syndrome | 7 (43.8) | 7 (43.8) | 0 | 0 | 1 (14.3) | 1 (14.3) | 1 (12.5) | 1 (12.5) | 9 (24.3) | 9 (24.3) |
| Vomiting | 5 (31.3) | 0 | 0 | 0 | 1 (14.3) | 0 | 1 (12.5) | 0 | 7 (18.9) | 0 |
| Diarrhoea | 4 (25.0) | 0 | 0 | 0 | 0 | 0 | 2 (25.0) | 0 | 6 (16.2) | 0 |
| Fatigue | 4 (25.0) | 0 | 0 | 0 | 0 | 0 | 2 (25.0) | 0 | 6 (16.2) | 0 |
| Asthenia | 2 (12.5) | 0 | 1 (16.7) | 0 | 0 | 0 | 2 (25.0) | 0 | 5 (13.5) | 0 |
| Pyrexia | 3 (18.8) | 0 | 0 | 0 | 1 (14.3) | 0 | 0 | 0 | 4 (10.8) | 0 |
| White Blood Cell Count Decreased | 1 (6.3) | 0 | 0 | 0 | 1 (14.3) | 1 (14.3) | 2 (25.0) | 2 (25.0) | 4 (10.8) | 3 (8.1) |
| Amylase Increased | 3 (18.8) | 0 | 0 | 0 | 0 | 0 | 0 | 0 | 3 (8.1) | 0 |
| Lipase Increased | 3 (18.8) | 2 (12.5) | 0 | 0 | 0 | 0 | 0 | 0 | 3 (8.1) | 2 (5.4) |
| Acute Kidney Injury | 1 (6.3) | 0 | 1 (16.7) | 1 (16.7) | 1 (14.3) | 0 | | | 3 (8.1) | 1 (2.7) |
| Blood Creatinine Increased | 1 (6.3) | 0 | 0 | 0 | 1 (14.3) | 0 | 1 (12.5) | 1 (12.5) | 3 (8.1) | 1 (2.7) |
| Blood Phosphorus Increased | 1 (6.3) | 0 | 1 (16.7) | 0 | 0 | 0 | 0 | 0 | 3 (8.1) | 0 |
| Hyperbilirubinaemia | 1 (6.3) | 0 | 1 (16.7) | 0 | 1 (14.3) | 0 | 0 | 0 | 3 (8.1) | 0 |
| Hyperphosphataemia | 1 (6.3) | 0 | 1 (16.7) | 0 | 0 | 0 | 1 (12.5) | 0 | 3 (8.1) | 0 |
| Abdominal Pain | 2 (12.5) | 0 | 0 | 0 | 0 | 0 | 0 | 0 | 2 (5.4) | 0 |
| Atrial Fibrillation | 2 (12.5) | 0 | 0 | 0 | 0 | 0 | 0 | 0 | 2 (5.4) | 0 |
| Blood Bilirubin Increased | 1 (6.3) | 0 | 1 (16.7) | 0 | 0 | 0 | 0 | 0 | 2 (5.4) | 0 |
| C-Reactive Protein Increased | 1 (6.3) | 0 | 0 | 0 | 1 (14.3) | 1 (14.3) | 0 | 0 | 2 (5.4) | 1 (2.7) |
| Constipation | 0 | 0 | 1 (16.7) | 0 | | | 1 (12.5) | 0 | 2 (5.4) | 0 |
| Dyspepsia | 1 (6.3) | 0 | 0 | 0 | 1 (14.3) | 0 | 0 | 0 | 2 (5.4) | 0 |
| Gamma-Glutamyltransferase Increased | 2 (12.5) | 1 (6.3) | 0 | 0 | 0 | 0 | 0 | 0 | 2 (5.4) | 1 (2.7) |
| General Physical Health Deterioration | 2 (12.5) | 0 | 0 | 0 | 0 | 0 | 0 | 0 | 2 (5.4) | 0 |
| Gingival Bleeding | 2 (12.5) | 0 | 0 | 0 | 0 | 0 | 0 | 0 | 2 (5.4) | 0 |
| Headache | 1 (6.3) | 0 | 1 (16.7) | 0 | 0 | 0 | 0 | 0 | 2 (5.4) | 0 |
| Hyperuricaemia | 2 (12.5) | 1 (6.3) | 2 (33.3) | 0 | 1 (14.3) | 0 | 2 (5.4) | 1 (2.7) | | |
| Hypocalcaemia | 2 (12.5) | 0 | 0 | 0 | 0 | 0 | 0 | 0 | 2 (5.4) | 0 |
| Hypophosphataemia | 2 (12.5) | 2 (12.5) | 0 | 0 | 0 | 0 | 0 | 0 | 2 (5.4) | 2 (5.4) |
| Hyponatraemia | 1 (6.3) | 0 | 1 (16.7) | 0 | 0 | 0 | 0 | 0 | 2 (5.4) | 0 |
| Leukopenia | 2 (12.5) | 2 (12.5) | 0 | 0 | 0 | 0 | 0 | 0 | 2 (5.4) | 2 (5.4) |

TABLE 4-continued

All grades and grade 3/4 adverse events, suspected to be study drug related, by preferred term and regimens-hematological tumors

| | HDM201 Regimen 1A subjects N = 16 | | HDM201 Regimen 1B subjects N = 6 | | HDM201 Regimen 2A Subjects N = 7 | | HDM201 Regimen 2C subjects N = 8 | | All subjects N = 37 | |
|---|---|---|---|---|---|---|---|---|---|---|
| MEDDRA Preferred Term | All Grades n (%) | Grade 3/4 n (%) | All Grades n (%) | Grade 3/4 n (%) | All Grades n (%) | Grade 3/4 n (%) | All Grades n (%) | Grade 3/4 n (%) | All Grades n (%) | Grade 3/4 n (%) |
| Malaise | 1 (6.3) | 0 | 0 | 0 | 1 (14.3) | 0 | 0 | 0 | 2 (5.4) | 0 |
| Mouth Haemorrhage | 2 (12.5) | 0 | 0 | 0 | 0 | 0 | 0 | 0 | 2 (5.4) | 0 |
| Pancytopenia | 0 | 0 | 1 (16.7) | 1 (16.7) | 0 | 0 | 1 (12.5) | 1 (12.5) | 2 (5.4) | 2 (5.4) |
| Stomatitis | 1 (6.3) | 1 (6.3) | 0 | 0 | 0 | 0 | 1 (12.5) | 0 | 2 (5.4) | 1 (2.7) |
| Abdominal Discomfort | 1 (6.3) | 0 | 0 | 0 | 0 | 0 | 0 | 0 | 1 (2.7) | 0 |
| Abdominal Pain Upper | 1 (6.3) | 0 | 0 | 0 | 0 | 0 | 0 | 0 | 1 (2.7) | 0 |
| Arthralgia | 1 (6.3) | 0 | 0 | 0 | 0 | 0 | 0 | 0 | 1 (2.7) | 0 |
| Atypical Pneumonia | 1 (6.3) | 0 | 0 | 0 | 0 | 0 | 0 | 0 | 1 (2.7) | 0 |
| Balanitis Candida | 1 (6.3) | 0 | 0 | 0 | 0 | 0 | 0 | 0 | 1 (2.7) | 0 |
| Blood Alkaline Phosphatase Increased | 1 (6.3) | 0 | 0 | 0 | 0 | 0 | 0 | 0 | 1 (2.7) | 0 |
| Blood Uric Acid Increased | 1 (6.3) | 1 (6.3) | 0 | 0 | 0 | 0 | 0 | 0 | 1 (2.7) | 1 (2.7) |
| Bone Marrow Failure | 0 | 0 | 0 | 0 | 1 (14.3) | 1 (14.3) | 0 | 0 | 1 (2.7) | 1 (2.7) |
| Cardiac Failure | 1 (6.3) | 0 | 0 | 0 | 0 | 0 | 0 | 0 | 1 (2.7) | 0 |
| Cellulitis | 0 | 0 | 1 (16.7) | 1 (16.7) | 0 | 0 | 0 | 0 | 1 (2.7) | 1 (2.7) |
| Chronic Graft Versus Host Disease | 1 (6.3) | 1 (6.3) | 0 | 0 | 0 | 0 | 0 | 0 | 1 (2.7) | 1 (2.7) |
| Conjunctival Haemorrhage | 1 (6.3) | 0 | 0 | 0 | 0 | 0 | 0 | 0 | 1 (2.7) | 0 |
| Cough | 1 (6.3) | 0 | 0 | 0 | 0 | 0 | 0 | 0 | 1 (2.7) | 0 |
| Cystitis Viral | 1 (6.3) | 0 | 0 | 0 | 0 | 0 | 0 | 0 | 1 (2.7) | 0 |
| Cytomegalovirus Infection | 0 | 0 | 0 | 0 | 1 (14.3) | 0 | 0 | 0 | 1 (2.7) | 0 |
| Dyspnoea | 1 (6.3) | 1 (6.3) | 0 | 0 | 0 | 0 | 0 | 0 | 1 (2.7) | 1 (2.7) |
| Epistaxis | 0 | 0 | 0 | 0 | 0 | 0 | 1 (12.5) | 0 | 1 (2.7) | 0 |
| Graft Versus Host Disease | 1 (6.3) | 0 | 0 | 0 | 0 | 0 | 0 | 0 | 1 (2.7) | 0 |
| Haemoglobin Decreased | 1 (6.3) | 0 | 0 | 0 | 0 | 0 | 0 | 0 | 1 (2.7) | 0 |
| Hyperglycaemia | 1 (6.3) | 0 | 0 | 0 | 0 | 0 | 0 | 0 | 1 (2.7) | 0 |
| Hyperkalaemia | 0 | 0 | 1 (16.7) | 1 (16.7) | 0 | 0 | 0 | 0 | 1 (2.7) | 1 (2.7) |
| Hypoalbuminaemia | 1 (6.3) | 0 | 0 | 0 | 0 | 0 | 0 | 0 | 1 (2.7) | 0 |
| Hypomagnesaemia | 1 (6.3) | 0 | 0 | 0 | 0 | 0 | 0 | 0 | 1 (2.7) | 0 |
| Hypokalaemia | 0 | 0 | 1 (16.7) | 0 | 0 | 0 | 0 | 0 | 1 (2.7) | 0 |
| Hypotension | 1 (6.3) | 0 | 0 | 0 | 0 | 0 | 0 | 0 | 1 (2.7) | 0 |
| Infection | 1 (6.3) | 1 (6.3) | 0 | 0 | 0 | 0 | 0 | 0 | 1 (2.7) | 1 (2.7) |
| Infective Glossitis | 0 | 0 | 0 | 0 | 0 | 0 | 1 (12.5) | 0 | 1 (2.7) | 0 |
| Influenza Like Illness | 1 (6.3) | 0 | 0 | 0 | 0 | 0 | 0 | 0 | 1 (2.7) | 0 |
| Iron Overload | 1 (6.3) | 0 | 0 | 0 | 0 | 0 | 0 | 0 | 1 (2.7) | 0 |
| Lip Oedema | 1 (6.3) | 0 | 0 | 0 | 0 | 0 | 0 | 0 | 1 (2.7) | 0 |
| Macular Oedema | 0 | 0 | 1 (16.7) | 1 (16.7) | 0 | 0 | 0 | 0 | 1 (2.7) | 1 (2.7) |
| Oedema | 1 (6.3) | 0 | 0 | 0 | 0 | 0 | 0 | 0 | 1 (2.7) | 0 |
| Oedema Peripheral | | | 1 (16.7) | 0 | 0 | 0 | 0 | 0 | 1 (2.7) | 0 |
| Oral Disorder | 1 (6.3) | 0 | 0 | 0 | 0 | 0 | 0 | 0 | 1 (2.7) | 0 |
| Pain In Extremity | 1 (6.3) | 0 | 0 | 0 | 0 | 0 | 0 | 0 | 1 (2.7) | 0 |
| Pneumonia | 1 (6.3) | 0 | 0 | 0 | 0 | 0 | 0 | 0 | 1 (2.7) | 0 |
| Pollakiuria | 1 (6.3) | 0 | 0 | 0 | 0 | 0 | 0 | 0 | 1 (2.7) | 0 |

TABLE 4-continued

All grades and grade 3/4 adverse events, suspected to be study drug related,
by preferred term and regimens-hematological tumors

| MEDDRA Preferred Term | HDM201 Regimen 1A subjects N = 16 | | HDM201 Regimen 1B subjects N = 6 | | HDM201 Regimen 2A Subjects N = 7 | | HDM201 Regimen 2C subjects N = 8 | | All subjects N = 37 | |
|---|---|---|---|---|---|---|---|---|---|---|
| | All Grades n (%) | Grade 3/4 n (%) | All Grades n (%) | Grade 3/4 n (%) | All Grades n (%) | Grade 3/4 n (%) | All Grades n (%) | Grade 3/4 n (%) | All Grades n (%) | Grade 3/4 n (%) |
| Rash | 1 (6.3) | 0 | 0 | 0 | 0 | 0 | 0 | 0 | 1 (2.7) | 0 |
| Rash Erythematous | 1 (6.3) | 0 | 0 | 0 | 0 | 0 | 0 | 0 | 1 (2.7) | 0 |
| Rash Papular | 1 (6.3) | 0 | 0 | 0 | 0 | 0 | 0 | 0 | 1 (2.7) | 0 |
| Rectal Haemorrhage | 0 | 0 | 1 (16.7) | 0 | 0 | 0 | 0 | 0 | 1 (2.7) | 0 |
| Renal Failure | 0 | 0 | 0 | 0 | 0 | 0 | 1 (12.5) | 1 (12.5) | 1 (2.7) | 1 (2.7) |
| Skin Exfoliation | 1 (6.3) | 0 | 0 | 0 | 0 | 0 | 0 | 0 | 1 (2.7) | 0 |
| Subarachnoid Haemorrhage | 1 (6.3) | 1 (6.3) | 0 | 0 | 0 | 0 | 0 | 0 | 1 (2.7) | 1 (2.7) |
| Weight Decreased | 1 (6.3) | 0 | 0 | 0 | 0 | 0 | 0 | 0 | 1 (2.7) | 0 |

Preferred terms are sorted in descending frequency of <all grades> column, as reported in the <All subjects> column.
A subject with multiple occurrences of an AE under one treatment is counted only once in the AE category For that treatment.
A subject with multiple adverse events is counted only once in the total row.
Only AEs occurring during treatment or within 30 days of the last study medication are reported.

Anti-Tumor Activity/Efficacy of Regimen 1B in Hematological Tumors

Figure 6:
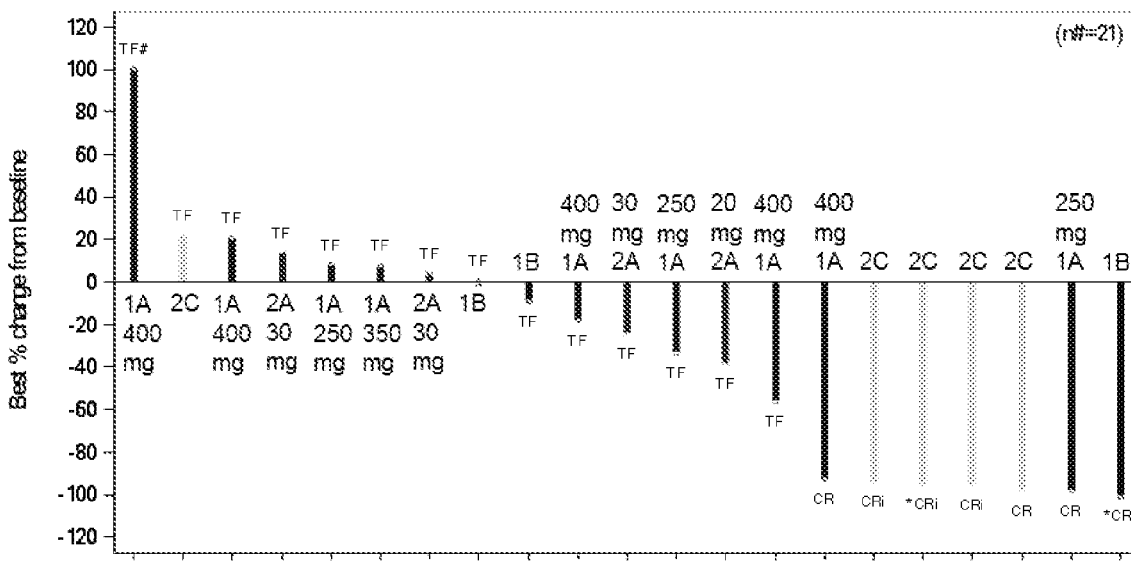
FIG. 6 illustrates the best percentage change in blast percentage in bone marrow (BM) aspirate in AML patients (patients with available bone marrow aspirate).
*Ongoing treatment; #best percentage change is ≥100; TF: treatment failure; CR: complete response; CRi: morphologic CR with incomplete blood count recovery. Daily doses: Regimen 1A: 250, 350 or 400 mg. Regimen 1B: 150 mg. Regimen 2A: 20, 30 mg. Regimen 2C: 45 mg.

Tables 5 and 6 and FIG. 6 provide efficacy information for dosing regimen 1B in comparison to other regimens. One patient treated following the regimen 1B showed a CRi and thus demonstrated regimen 1B as being effective also in hematological tumors. In the best percentage change in blast percentage in bone marrow (BM) aspirate (FIG. 6) this CRi patient showed the strongest positive effect.

TABLE 5a

Anti-tumor activity (March 2017)

| BOR, n (%) | Regimen 1A (n = 15) | Regimen 1B (n = 6) | Regimen 2A (n = 7) | Regimen 2C (n = 7) | Total (N = 35) |
|---|---|---|---|---|---|
| CR | 2 (13) | 0 (0) | 0 (0) | 1 (14) | 3 (9) |
| CRi | 0 (0) | 1 (17) | 0 (0) | 3 (43) | 4 (11) |
| ORR (CR + CRi + PR) | 2 (13) | 1 (17) | 0 (0) | 4 (57) | 7 (20) |

BOR, best overall response;
CR, complete response;
CRi, morphologic CR with incomplete blood count recovery;
ORR, overall response rate TABLE 5b Anti-tumor activity (September 2017)

| | Regimen 1A | Regimen 1B | Regimen 2A | Regimen 2C |
|---|---|---|---|---|
| Dose escalation | 250 mg (3): 1 CR 350 mg (4): — 400 mg (9): 1 CR | 150 mg (6): 1 CRi 120 mg (6): 1 CR | 3 pts, 20 mg (3): — 4 pts: 30 mg (4): — | 45 mg (8): 1 CR, 3 CRi |
| Dose expansion | 6 pts, 250 mg: 1 CRi | (expansion not started yet) | (no expansion) | 45 mg (17): 1 CR, 1CRi |

Number in brackets, number of patients, patients;
CR, complete response;
CRi, morphologic CR with incomplete blood count recovery TABLE 6a Characteristics of AML patients with CR/CRi (March 2017)

| Regimen | Dose | Age (years) | Cytogenetics at diagnosis | Time to CR/CRi (weeks) | Count recovery time from C1D1 (days) | Duration of CR/CRi (days) |
|---|---|---|---|---|---|---|
| CR patients |
| High-dose: 1A | 250 mg | 81 | Intermediate | 7 | 48 | 50 |
| High-dose: 1A | 400 mg | 71 | Intermediate | 6 | 40 | 23 |
| Low-dose: 2C | 45 mg | 75 | Missing | 5 | 32 | 152 |
| CRi patients |
| High-dose: 1B | 150 mg | 83 | Intermediate | 11 | NA | 51 |
| Low-dose: 2C | 45 mg | 80 | Missing | 7 | NA | 40 |
| Low-dose: 2C | 45 mg | 70 | Unfavorable | 12 | NA | 1* |
| Low-dose: 2C | 45 mg | 79 | Intermediate | 4 | NA | 1† |

*Patient withdrew consent while on CRi
†Patient ongoing at the time of data cut off TABLE 6b Updated table (September 2017), characteristics of AML patients with CR/CRi

| | Regimen | HDM dose | Sex/Age | WHO classification at initial diagnosis | Time to CR/CRI (weeks) | Count recovery time from C1D1 (days) | Duration of CR/CRi (days) |
|---|---|---|---|---|---|---|---|
| CR achieved with HDM201 | Reg 1A | 250 mg | Female/81 | AML with MDS related changes | 7 | 48 | 50 |
| | Reg 1A | 400 mg | Male/71 | AML | 6 | 40 | 23 |
| | Reg 1B | 120 mg | Male/67 | AML | 4 | 28 | 45 |
| | Reg 2C | 45 mg | Male/76 | AML | 5 | 32 | 152 |
| | Reg 2C | 45 mg | Female/71 | AML with MDS related changes | 4 | 30 | 41 |
| CRi achieved with HDM201 | Reg 1B | 150 mg | Female/83 | AML with MDS related changes | 11 | NA | 51 |
| | Reg 1A | 250 mg | Female/73 | AML | 3 | NA | 67 |
| | Reg 2C | 45 mg | Female/80 | AML with multilingeage dysplasia | 7 | NA | 40 |
| | Reg 2C | 45 mg | Male/70 | AML | 12 | NA | 1 |
| | Reg 2C | 45 mg | Male/79 | AML with MDS related changes | 4 | NA | 62 |
| | Reg 2C | 45 mg | Female/72 | AML with multilingeage dysplasia | 4 | NA | 105 |

The already observed 2 CR/CRi results out of the small number of patients treated so far demonstrate the strong antitumor activity of the HDM201 in AML patients when dosed according to Regimen 1B.

Clinical PK

Pharmacokinetic data have been evaluated throughout the course of the clinical study. Non-compartmental PK analysis showed a median time to reach maximum plasma concentrations ranging from 2.0 to 5.8 h across the dose range (2 to 350 mg). A preliminary dose proportionality assessment showed approximately dose proportional PK (AUClast and Cmax) over the dose range studied. For the majority of dose cohorts, the inter-patient variability (CV % Geo-mean) for AUClast and Cmax was low to moderate (6 to 58.5%). Furthermore, an integrated analysis of all available HDM201 concentrations was conducted using a population approach. The PK of HDM201 was best described by a 1-compartment PK model with a delayed zero- and first-order absorption process, and a linear clearance. Body weight was identified as a statistically significant covariate on apparent central volume of distribution (Vc/F), in which Vc/F increased with increasing body weight.

Figure 7:
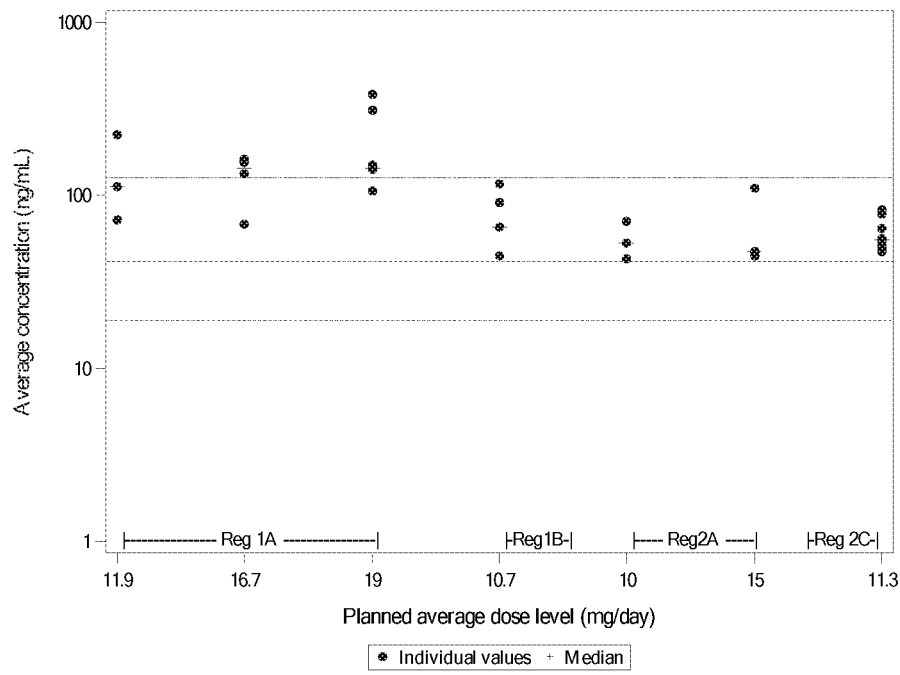
FIG. 7 shows the individual average concentration during first treatment cycle versus dose per regimen for patients with hematological tumors.

Compartmental PK modeling was used to estimate the individual average concentration during cycle 1 for patients with hematological tumors treated following the four different (FIG. 7). For all patients with measured PK, the estimated average drug concentrations during cycle 1 were above the most conservative average tumor stasis concentration of about 41 ng/mL per cycle determined from PKPD modeling of preclinical data (human SJSA-1 xenograft rat model).

The invention claimed is:

1. A method for treating cancer in patients in need thereof which comprises administering an effective amount of an HDM2-p53 interaction inhibitor which is HDM201,
   wherein a daily dose of the inhibitor is administered on two different administration days within a treatment cycle,
   wherein the first administration day and second administration day are interrupted by a short administration-free period, and the second administration day of the first or earlier treatment cycle and the first administration of the following cycle are interrupted by a long administration-free period,
wherein the short administration-free period is composed of from 4 to 8 days, and the long administration-free period is composed of from 13 to 27 days, and
wherein the treatment is composed of at least 2 treatment cycles.

2. The method of claim 1, wherein the short administration-free period is composed of from 4 to 8 days, and the long administration-free period is composed of from 18 to 22 days.

3. The method of claim 1, wherein the short administration-free period is composed of from 5 to 7 days, and the long administration-free period is composed of from 19 to 21 days.

4. The method of claim 1, wherein the short administration-free period is composed of 6 days, and the long administration-free period is composed of from 20 days.

5. The method of claim 1, wherein said inhibitor is HDM201 succinic acid.

6. The method of claim 1 wherein the daily dose on the administration days is from 100 mg to 200 mg.

7. The method of claim 1, wherein the daily dose on the administration days is from 100 mg to 150 mg.

8. The method of claim 1, wherein the daily dose on the administration days is 120 mg.

9. The method of claim 1, wherein the cancer is a TP53 wild-type tumor.

10. The method of claim 1, wherein the cancer is a solid tumor.

11. The method of claim 10, wherein the solid tumor is selected from sarcomas, liposarcoma, soft tissue sarcoma, melanomas, skin melanoma, uveal melanoma, blastomas, neuroblastoma, colon tumor, colorectal tumor, kidney tumor, and livertumor.

12. The method of claim 1, wherein said inhibitor is administered in combination with a thrombopoietin receptor agonist.

13. The method of claim 12, wherein the thrombopoietin receptor agonist is eltrombopag.

14. The method of claim 1, wherein the treatment reduces the risk of hematologicaltoxicities.

15. The method of claim 14, wherein the hematological toxicities are selected from the group consisting of thrombocytopenia, neutropenia, leucopenia, lymphopenia, or anemia.

16. The method of claim 14, wherein the hematological toxicity is thrombocytopenia.

17. The method of claim 1, wherein the cancer is a hematological tumor.

18. The method of claim 17, wherein the hematological tumor is aleukemia.

19. The method of claim 17, wherein the hematological tumor is selected from acute myeloid leukemia (AML), myelodysplastic syndrome (MDS), and acute lymphoblasticleukemia (ALL).

20. The method of claim 17, wherein the hematological tumor is a relapsed/refractory hematological tumor.

* * * * *